(12) United States Patent
Urban et al.

(10) Patent No.: US 7,854,941 B2
(45) Date of Patent: Dec. 21, 2010

(54) METHOD OF ATTACHING DRUG COMPOUNDS TO NON-REACTIVE POLYMER SURFACES

(75) Inventors: Marek W. Urban, Hattiesburg, MS (US); Nattharika Aumsuwan, Hattiesburg, MS (US)

(73) Assignee: The University of Southern Mississippi, Hattiesburg, MS (US)

( * ) Notice: Subject to any disclaimer, the term of this patent is extended or adjusted under 35 U.S.C. 154(b) by 429 days.

(21) Appl. No.: 12/069,726

(22) Filed: Feb. 12, 2008

(65) Prior Publication Data

US 2008/0207535 A1 Aug. 28, 2008

Related U.S. Application Data

(60) Provisional application No. 60/900,810, filed on Feb. 12, 2007.

(51) Int. Cl.
*A61F 3/00* (2006.01)
*A61F 21/00* (2006.01)
(52) U.S. Cl. .................................. 424/423; 424/422
(58) Field of Classification Search .................. None
See application file for complete search history.

(56) References Cited

U.S. PATENT DOCUMENTS

| | | | | |
|---|---|---|---|---|
| 4,442,133 | A | 4/1984 | Greco et al. | 427/2.25 |
| 5,364,662 | A | 11/1994 | Domenico et al. | 427/536 |
| 6,096,070 | A | 8/2000 | Ragheb et al. | 623/1.39 |
| 6,129,757 | A | 10/2000 | Weadock | 623/1.39 |
| 6,168,619 | B1 | 1/2001 | Dinh et al. | 623/1.13 |
| 6,306,165 | B1 | 10/2001 | Patnaik et al. | 623/1.43 |
| 6,328,762 | B1 | 12/2001 | Anderson et al. | 623/1.41 |
| 6,358,557 | B1 | 3/2002 | Wang et al. | 427/2.24 |
| 6,803,069 | B2 | 10/2004 | Patnaik et al. | 427/2.24 |
| 2002/0082679 | A1 | 6/2002 | Sirhan et al. | 623/1.15 |
| 2005/0283224 | A1 | 12/2005 | King | 623/1.43 |
| 2006/0286140 | A1 | 12/2006 | Wickstrom et al. | 424/423 |

FOREIGN PATENT DOCUMENTS

| | | |
|---|---|---|
| WO | WO 99/42080 A2 | 8/1999 |
| WO | WO 03/092727 A1 | 11/2003 |
| WO | WO 2004/012783 A1 | 2/2004 |
| WO | WO 2004/026361 A1 | 4/2004 |
| WO | WO 2004/093794 A2 | 11/2004 |
| WO | WO 2005/069889 A2 | 8/2005 |
| WO | WO 2006/026325 A2 | 3/2006 |

OTHER PUBLICATIONS

Gaboury SR and Urban MW (1993), *Langmuir*. 9:3225-3233.
Bae W-S and Urban MW (2004), *Langmuir*. 20:8372-8378.
Zhao Y and Urban MW (1999), *Langmuir*. 15:3538-3544.
Kim H and Urban MW (1996), *Langmuir*. 12:1047-1050.
Kim H and Urban MW (1996), *Langmuir*. 12:1051-1055.
Kim H and Urban MW (1996), *Langmuir*. 12:3282-3288.
Kim H and Urban MW (1999), *Langmuir*. 15:3499-3505.
Aumsuwan N et al. (2007), *Biomacromolecules*. 8:713-718.
Konig W (2005), Interaction of biopolymers with antimicrobial compounds—immunomodulation of human effector cells, *45th ICAAC, A meeting of the American Society of Microbiology*, (Session 5, Paper B-42), 3 pages.
Darouiche RO and Mansouri MD (2004), *Ann. Vasc. Surg.* 18:497-501.
Hendricks SK et al. (1999), *J. Biomed. Mater. Res.* 50:160-170.

*Primary Examiner*—Elli Peselev
(74) *Attorney, Agent, or Firm*—Howrey LLP

(57) ABSTRACT

Polymers are disclosed that are chemically modified to retard bacterial growth. Such modified polymers (e.g. ePTFE and polypropylene) are produced by first creating acid groups on the polymer surface through reactions with an anhydride. The acid groups are then linked to polyethylene glycol (PEG) through esterification or other reactions such as amidation. Preferably, at least two different molecular weight PEG species are employed. The antimicrobial surface is completed by linking antibiotics (e.g. β-lactam antibiotics) to the PEG extensions. One preferred embodiment of such a modified polymer is produced using ePTFE, maleic anhydride (MA), and penicillin (PEN) to yield PEN-PEG-MA-ePTFE, which inhibits gram-positive bacteria. The PEG spacer is critical for PEN function in this context, since PEN-ePTFE is ineffective against bacterial growth. Another preferred embodiment incorporates ampicillin (AMP) and a heterobifunctional PEG, $HOOC-(CH_2-CH_2-O)_n-NH_2$, to yield AMP-PEG-MA-ePTFE. This latter example inhibits both gram-negative and gram-positive bacteria.

30 Claims, 13 Drawing Sheets

(A) Unmodified ePTFE  5 μm (B) Plasma reacted ePTFE  5 μm (C) Plasma reacted ePTFE with MA  5 μm (A) ePTFE 10 μm (B) MA-ePTFE 10 μm (C) PEG-MA-ePTFE 10 μm (a)

(b)

METHOD OF ATTACHING DRUG COMPOUNDS TO NON-REACTIVE POLYMER SURFACES

This application claims the benefit of priority to U.S. Provisional Application No. 60/900,810, filed Feb. 12, 2007, which is herein incorporated by reference in its entirety.

FIELD OF THE INVENTION

The invention relates to polymer compositions having modified surfaces, and methods of production thereof. In particular, the invention is directed to polymers, such as extended polytetrafluoroethylene (ePTFE), that have a surface modified to contain an antibiotic, such as penicillin. The invention also relates to polymers that have a surface modified with anhydride, polyethylene glycol (PEG) and an antibiotic. The invention can be employed to produce implantable medical devices that are resistant to microbial colonization.

BACKGROUND OF THE INVENTION

Development of materials, such as polymers, that can be utilized as implants or other devices that come in contact within the human body continues to be a major challenge. Although various polymers have found diversified biomedical applications, it is apparent that there is virtually no polymeric material available that does not require surface modifications to allow effective use thereof. By modifying polymer surfaces one may achieve a number of desirable properties ranging from blood clotting prevention to controllable drug release, and other applications, while maintaining useful bulk polymer properties.

A variety of polymers are being utilized in these and other biomedical applications; for example, polyvinyl chloride (PVC) is used in the manufacture of cardiac catheters, surgical tapes, artificial hearts, blood pumps and artificial limbs (Kroschwitz, 1989; Weber et al., 2003; Shalaby, 1994; Kim and Urban, 1998; DeHaan, 1971). In order to function properly in these devices, PVC requires specific surface modifications. Alternatively, polymethylmethacrylate (PMMA), which is utilized to produce contact lenses, bone cement, artificial teeth and dental fillings, requires different surface modifications in order to function properly (Pena et al., 1997; Andreopoulos et al., 1991; Frazer et al., 2005). Along the same lines, in order for polydimethylsiloxane (PDMS) to function properly as a component in contact lenses, artificial skin, oxygenators and certain drug delivery systems (Kroschwitz, 1989; Tokuyama et al., 2005; Schulze Nahrup et al, 2004; Niwa et al., 2001; Huck, 2005; Bae and Urban, 2004; Bae and Urban, 2006), it necessitates specific surface modifications that are different from those surface modifications required for the proper function of expanded polytetrafluoroethylene (ePTFE) in vascular graft prostheses, heart patches, and a stapes prosthesis (Kroschwitz, 1989; Swartbol et al., 1996; Renard et al., 1996; Kang et al., 1996; Jardine and Wilson, 2005; Dupuy et al., 2001; Catanese et al., 1999).

Regardless of specific surface modifications, all biomaterials are susceptible to bacterial colonization and growth, which can have detrimental effects on biomaterial. Thus, much effort has been made to generate polymeric surfaces with desirable bio-properties that exhibit antimicrobial activity. For example, a recent study by one of the inventors demonstrated that PDMS could be modified with amoxicillin, thereby rendering the PDMS surface as antimicrobial (Bae and Urban, 2006). Since ePTFE is a non-reactive and non-toxic fluoro-containing polymer, it has gained wide use in the medical field. For example, ePTFE can be incorporated in vascular grafts and mitral valve tendon replacements, and also finds application in orthopedic and reconstructive surgical practices (Rittgers et al., 1985; Mole, 1992; Bellon et al., 1993). However, when implanted into various biological environments, ePTFE performs similarly with other implanted polymeric materials insofar as bacterial colonization on the polymer surface is concerned (Johnell et al., 2005; Balazs et al., 2004); this problem remains a major obstacle to realizing the full potential of ePTFE polymer in biomedical and industrial applications.

SUMMARY OF THE INVENTION

The present invention is drawn towards methods and compositions regarding polymer surfaces modified with bio-active agents such as antibiotic reagents. The invention is further drawn to the uses of modified polymer surfaces provided by the inventive methods and compositions.

One embodiment of the present invention is directed to a method having the steps of providing a polymer (e.g. polyolefin), reacting the polymer with an anhydride to link anhydride groups to the polymer surface, hydrolyzing the polymer surface-linked anhydride groups to create polymer surface-linked carboxylic acid groups, reacting the polymer surface-linked carboxylic acid groups with polyalkylene glycol or functionalized polyethylene glycol (PEG) to link polyalkylene glycol or functionalized PEG to the polymer surface, and reacting the polymer surface-linked polyalkylene glycol or functionalized PEG with a bio-active agent to link the bio-active agent to the polymer surface. Such a method yields a polymer surface modified with the bio-active agent.

The above reacting step for linking the polyalkylene glycol or functionalized PEG to the polymer surface can be performed via esterification or amidation, for example. In preferred embodiments, polyalkylene glycol is esterified to surface-linked carboxylic acid groups, whereas functionalized PEG having an amine group at one end is linked to surface-linked carboxylic groups via an amidation reaction. Both these esterification or amidation reactions may optionally entail an intermediate step of forming an acid halide (e.g. acid chloride) before coupling the polyalkylene glycol or functionalized PEG spacer.

The functionalized PEG may terminate at either end with an amine group or a carboxylic acid group. An example of such a PEG has the formula ($COOH$—$PEG$-$NH_2$):

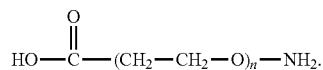

This functionalized PEG can participate in the above-described amidation reaction, wherein the amine end of this PEG is involved in amidation with surface-linked carboxylic acid groups.

The above reacting step for linking the bio-active agent, such as an antibiotic agent, to the surface-linked polyalkylene glycol or functionalized PEG can be performed either by esterification or amidation, for example. With esterifaction, skilled artisans would understand that the bio-active agent, if esterifying with surface-linked polyalkylene glycol groups, would do so through a carboxylic acid group of the bio-active agent. Alternatively, if the bio-active agent is to be linked to surface-linked functionalized PEG, the esterification may be between a hydroxyl group of the bio-active agent with a carboxylic acid group at the end of the surface linked functionalized PEG. This scenario would be the case if using COOH—PEG-NH$_2$ that is amidated to the surface-linked carboxylic acid group (i.e. the PEG's COOH group would be available for esterification).

For amidation of the bio-active agent (e.g. antibiotic agent) to surface-linked functionalized PEG (such as COOH—PEG-NH$_2$), this reaction may be performed such that (i) an amine group of the bio-active agent reacts with a carboxylic acid group at the end of the surface-linked functionalized PEG (e.g. COOH—PEG-NH$_2$ in which its amine group is involved in an amide bond with a surface-linked carboxylic acid group), or (ii) a carboxylic acid group of the bio-active agent reacts with an amine group at the end of the surface-linked functionalized PEG. Just as with the step of reacting the polyalkylene glycol or functionalized PEG with the surface-linked carboxylic acid groups, the esterification or amidation reactions for linking the bio-active agent to the surface-linked polyalkylene glycol or functionalized PEG spacers may involve the intermediate step of forming an acid halide such as acid chloride.

Multiple different embodiments of the above method are embraced by the current invention. Such embodiments optionally employ the following particular components, either alone or in combination: solid organic polymers such as ePTFE or polypropylene, β-lactam antibiotics such as penicillins or ampicillin, aminoglycoside antibiotics such as gentamicin, anhydrides that comprise a ring such as maleic anhydride, polymer surface-linked carboxylic acid groups, and a catalyst and coupling reagent. Further, the polyalkylene glycol, which may be PEG) and functionalized PEG may be incorporated in the present invention in two or more molecular weight forms, such as about 200 and about 600. The molecular weights of the polyalkylene glycol (e.g. PEG) or functionalized PEG may be in a range from about 100 to about 2000. Forms of functionalized PEG that may be incorporated in the invention are, for example, COOH—PEG-NH$_2$, monoglycidyl PEG, and/or diglycidyl PEG. Mixtures of polyalkylene glycols and functional PEGS may be employed.

Other embodiments of the above method comprise, alone or in combination, the following steps: reacting a polymer by placing the polymer in a chamber with an anhydride that is in the form of a plasma; modifying the polymer surface-linked acid groups to be acid halide groups such as acid chloride; reacting the polymer surface-linked polyalkylene glycol groups with an antibiotic agent by esterification; and monitoring the polymer surface after at least one the method steps by scanning electron microscopy analysis or attenuated total reflectance Fourier transform infrared (ATR-FTIR) spectral analysis.

A particular embodiment of the above inventive method incorporates the steps of providing ePTFE polymer, reacting the ePTFE with maleic anhydride to link maleic anhydride groups to the ePTFE surface, hydrolyzing the ePTFE surface-linked maleic anhydride groups to form ePTFE surface-linked carboxylic acid groups, modifying the ePTFE surface-linked carboxylic acid groups to be polymer surface-linked acid chloride groups, esterifying the ePTFE surface-linked acid chloride groups with PEG 200 and PEG 600 to link PEG groups to the ePTFE surface, and esterifying the ePTFE surface-linked PEG groups with a penicillin to link the penicillin to the ePTFE surface. Such a method yields ePTFE polymer having an antimicrobial surface.

Yet another embodiment of the current invention is directed to a polymer having a surface modified with a bio-active group. Such a surface may be antimicrobial, wherein the surface of the polymer is produced according to any one of the above-identified methods when incorporating an antibiotic group as the bio-active group. Such modified surfaces permit the use of antibiotics at a much lower concentration compared to that required when using regular antibiotic solutions.

One composition that embodies the present invention embraces a polymer having an antimicrobial surface that incorporates an organic linker group, a polyalkylene glycol spacer, and an antibiotic agent. The organic linker has at least two ester moieties and is covalently bonded to the polymer; at least two of the ester moieties of the linker are not involved in the linker-polymer covalent bond. The polyalkylene glycol spacer is in ester linkage to the organic linker group. The antibiotic agent is linked to the polyalkylene glycol spacer; this linkage is formed at the terminus of the polyalkylene glycol spacer that is not in linkage with the organic linker group. As per this arrangement of the aforementioned components, the antibiotic agent is located most distally from the polymer, thereby exposing the antibiotic agent to the external environment.

Multiple different embodiments of the above composition are embraced by the current invention. Such embodiments optionally incorporate the following particular components, either alone or in combination: ePTFE polymer, penicillin antibiotic, PEG 200 and 600, and an ester bond linking the antibiotic agent with the polyalkylene glycol spacer.

A particular embodiment of the above inventive composition embraces ePTFE polymer having an antimicrobial surface that incorporates an organic linker group, a PEG spacer, and a penicillin. The organic linker has four carbons and two ester moieties and is covalently bonded to the ePTFE; none of the ester moieties are involved in the linker-polymer covalent bond. The PEG spacer is in ester linkage to the organic linker group, and comprises both PEG 200 and PEG 600. The penicillin is ester-linked to the PEG spacer; this linkage is formed at the terminus of the PEG spacer that is not in linkage with the organic linker group. As per this arrangement of the aforementioned components, the penicillin is located most distally from the ePTFE, thereby exposing the penicillin to the external environment.

Another embodiment of the invention embraces a polymer having a surface modified with a bio-active agent. The components of the modified surface are an organic linker group, a polyalkylene glycol spacer, and a bio-active group. The organic linker group, which connects the polymer to the polyalkylene glycol spacer, has an ester moiety or an amide moiety. The organic linker group is covalently bonded to the polymer in such a way that neither the ester moiety nor the amide moiety participate in the covalent bond between the linker group and the polymer. The polyalkylene glycol spacer is in ester linkage or amide linkage to the organic linker group (this linkage accounts for the ester or amid moiety of the organic linker group). The bio-active group is in ester linkage or amide linkage to the polyalkylene glycol spacer; this ester or amide linkage between the bio-active group and polyalkylene glycol spacer is formed at the terminus of the polyalkylene glycol spacer that is not in linkage with the organic linker group. Thus, the bio-active group is located most distally from the polymer.

This polymer may comprise an organic polymer, such as ePTFE or polypropylene. The bio-active agent of the modified surface may be an antibiotic agent such as a β-lactam antibiotic (e.g. ampicillin or a penicillin) or an aminoglycoside antibiotic such as gentamicin. The polyalkylene glycol spacers may comprise two or more different molecular weights of polyalkylene glycol, which may be in the form of PEG (but where the terminal OH groups are involved in linkages). The polyalkylene glycol spacer, such as PEG, can have a molecular weight range between about 100 and 2000. All of the above features in the methods can apply to the composition.

DETAILED DESCRIPTION OF THE INVENTION

The current invention provides a solution to the problem of bacterial colonization and growth on the surface of polymers, such as ePTFE, when used in medically implanted devices. The invention is also applicable for preventing bacterial buildup (i.e. biofilms) on polymer-containing devices that are not implanted but that are also subject to conditions conducive to bacterial colonization. The current invention is a highly sought after advancement due to the fact that the normal operation of polymer-containing devices is severely hampered when a biofilm is produced thereupon; that the failure of some medical devices (e.g. catheters, artificial valves and joints) occurs after bacterial biofilm formation is of special concern given the consequent impact on patient health.

The current invention prevents the problematic growth of bacteria on polymeric surfaces via a novel approach of attaching antibiotic molecules to the polymer surface itself. The inventive process is exemplified in a non-limiting manner in FIG. 1 which illustrates surface modifications to ePTFE that ultimately lead to the attachment of penicillin (PEN). Penicillin is an antibiotic known for its ability to inhibit gram-positive bacterial growth (Strominger et al., 1959). Basically, surface microwave plasma reactions in the presence of an anhydride (maleic anhydride [MA] in FIG. 1) links the anhydride to the ePTFE polymer surface. Subsequent hydrolysis of the anhydride generates carboxylic acid groups (COOH), which are then esterified to polyethylene glycol (PEG). Finally, the extensions (spacers) formed by the PEG molecules are esterified to an antibiotic molecule (PEN in FIG. 1).

Figure 1:
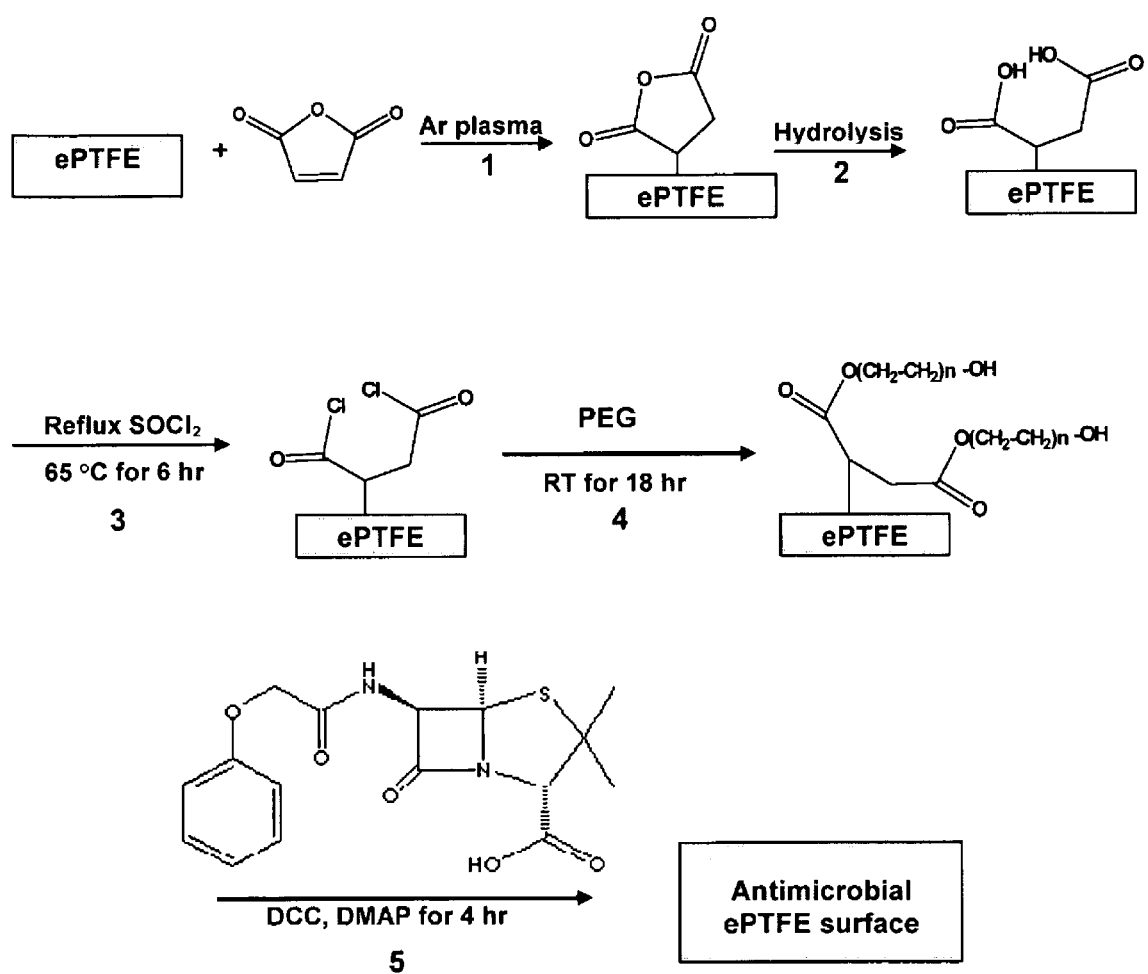
FIG. 1: Schematic diagram of surface reactions on ePTFE: step 1) microwave plasma reaction, step 2) hydrolysis of maleic anhydride (MA)/ePTFE to produce COOH acid groups, step 3) conversion of acid groups with halide, step 4) esterification of polyethylene glycol (PEG) to acid group, and step 5) esterification of penicillin (PEN) to PEG to yield PEN-PEG-MA-ePTFE.
Figure 2:
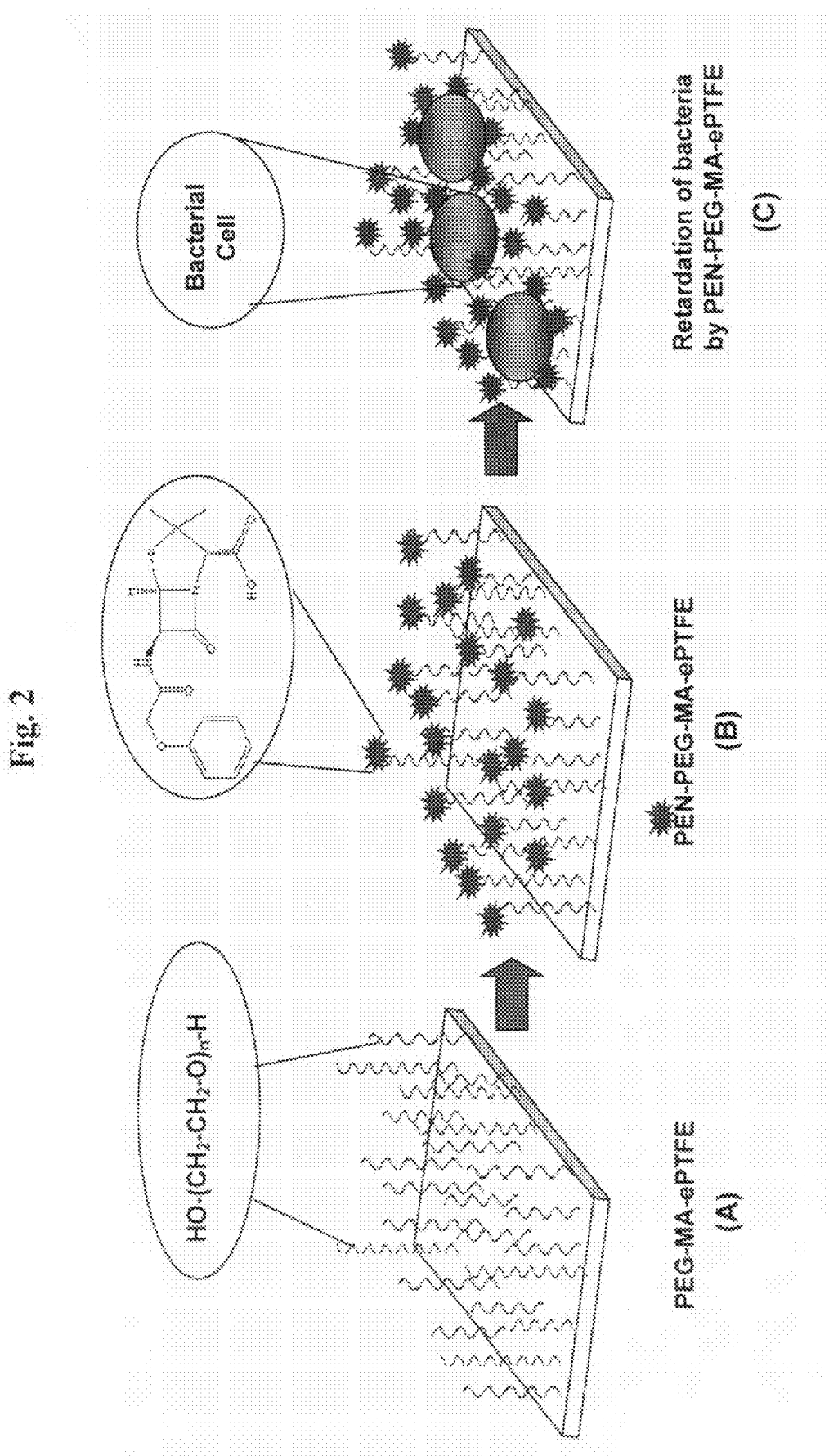
FIG. 2: Schematic diagram of surface-modified ePTFE compositions: A) PEG-MA-ePTFE, B) PEN-PEG-MA-ePTFE, and C) retardation of bacteria by PEN-PEG-MA-ePTFE.

Along with the novel process described above, the current invention also encompasses polymer compositions, such as for example those that are produced by the novel process, that contain an effective antibiotic surface layer. Such compositions are exemplified in a non-limiting manner in FIGS. 1 and 2. FIG. 1 (refer to product of step 4) depicts an embodiment of the invention wherein ePTFE polymer is linked to PEG via an organic linker having two ester groups. In this view, the organic linker is a maleic ester group that can be derived from maleic anhydride. FIG. 2A presents another view of an embodiment, wherein PEG molecules are shown to be linked to the ePTFE surface; this view does not show the organic linker group. In FIG. 2B, another embodiment of the invention is depicted wherein an antibiotic is linked to PEG molecules on the polymer surface; the PEG-antibiotic linkage may be in the form of an ester bond. An "antimicrobial surface" as used herein refers to such an embodiment, for example, whereby an antibiotic group is linked to the surface of polymer via at least a polyalkylene spacer such as PEG. Although the examples and figures of the instant application relate to the surface attachment of antibiotic agents, skilled artisans would readily acknowledge that other bio-active agents could be similarly attached onto a polymer surface using the disclosed methodology.

Several types of polymers may be incorporated into the inventive method and composition. Preferably, the polymers selected for the surface modifications described herein are solid compositions. The polymer substrate can be of any suitable form or shape, including but not limited to tubes, sheets, fibers, strips, films, plates, filaments, pellets, powders, and extruded, molded or cast articles. Further, the polymer substrate can be in the form of medical devices such as catheters and drains, or industrial devices such as spigots and pipes. The polymer substrate can be hydrophobic or hydrophilic, either property of which may be selected for specific downstream uses of the polymer.

Hydrophobic polymers useful in the present invention include but are not limited to solid synthetic or natural polymer materials. The polymer substrate preferably is a solid, but the invention can include other suitable substrates, for example, cross-linked hydrogels. The preferred solid polymer materials include, but are not limited to: polyolefins, such as polyethylene and polypropylene, polybutylene, polyisobutylene and ethylene-alphaolefin copolymers; silicone polymers; acrylic polymers and copolymers, including for example polyacrylonitrile, polymethylmethacrylate, polyethylmethacrylate, polyethylacrylate, and other polyesteracrylates and polyestermethacrylates; fluoropolymers, such as polytetrafluoroethylene, extended polytetrafluoroethylene, chlorotrifluoroethylene, fluorinated ethylene-propylene, polyvinylfluoride and polyvinylidenefluoride; vinyl polymers, such as polyvinylchloride, polyvinylmethylether, polystyrene, polyvinylacetate, and polyvinyl ketones; vinyl monomer-containing copolymers, such as acrylonitrile butadiene styrene (ABS); natural and synthetic rubbers, including for example latex rubber, butadiene-styrene copolymer, polyisoprene, polybutadiene, butadiene-acrylonitrile copolymers, polychloroprene polymers, polyisobutylene rubber, ethylene-propylenediene copolymers, and polyisobutylene-isoprene; polyurethanes, such as polyetherurethanes, polyesterurethanes, polycarbonateurethanes and polysiloxaneurethanes; and polyamides, such as Nylon 6, Nylon 66, Nylon 10, and Nylon 11; polyesters; epoxy polymers; wool; cotton; silk; rayon; cellulose; and modified celluloses. Combinations of any of the aforementioned polymers can also be used in the present invention. It is obvious from this list that the invention preferably incorporates an organic polymer.

Hydrophilic polymers that can be incorporated in the present invention include, but are not limited to: hydrophilic acrylic polymers such as polyacrylamide, poly-2-hydroxyethylacrylate, poly-N,N'-dimethylacrylamide, polyacrylic acid, and polymethacrylic acid; vinyl polymers, including for example poly-N-vinylpyrrolidone and polyvinylpyridine; polymaleic acid; poly-2-hydroxyethyl fumarate; starch and polyvinyl alcohol. Combinations of any of the aforementioned polymers can also be used in the present invention.

Certain of the above-mentioned polymers are particularly better at serving in one capacity compared to another capacity (e.g. medical versus industrial). It is well within the normal skill in the art to recognize which polymers, co-polymers, and combinations thereof are suitable for specific purposes.

Anhydrides are employed in the inventive method and may also be used in fabricating the inventive composition of a polymer having an antimicrobial surface. In this latter context, an anhydride molecule may be useful for forming the "organic linker group" which is used as a bridge between the polymer surface and the polyalkylene spacers (refer below). A benefit for using this group of organic molecules is their simple modification by hydrolysis to yield at least two carboxylic acid groups which can be used to produce the "ester moieties" of the organic linker that result when polyalkylene spacer groups are conjugated to the organic linker. Once anhydride is linked to the polymer, it is likely that the carboxylic acid groups formed by hydrolysis are "branched" out from the polymer surface; this results since the covalent bond (formed by a plasma reaction, refer below) linking the polymer to the anhydride is likely made to a carbon located between the anhydride group. For example, with maleic anhydride, the polymer-anhydride bond would be made to either carbon forming the C=C double-bond in the maleic anhydride ring. Therefore, such branching would not accompany polymer linkage to acetic anhydride. Though the application should not be held to any particular theory, one benefit of the aforementioned branching effect may be due to its influence on positioning of the polyalkylene spacer molecules; such positioning may allow the linear spacers to project perpendicularly away from the polymer surface. This non-limiting idea is conceptualized in FIG. 2A.

It is of interest to note that the abovementioned polymer-anhydride bond is a covalent bond. Though the exact mechanism for forming this covalent bond is incompletely understood, previous work whereby anhydride was linked to PDMS via a plasma-driven reaction demonstrated that a carbon-carbon (C—C) bond constituted the PDMS-anhydride linkage (Gaboury and Urban, 1993; herein incorporated by reference in its entirety). Given the similar chemistry between this previous example and the reactions embraced by the current application, the bond formed between an anhydride and a polymer such as ePTFE is very likely a C—C bond, when the bonding reaction is plasma-driven.

Preferably the anhydrides employed to practice the current invention are organic anhydrides. An organic anhydride is a chemical containing the functional group:

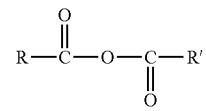

in which R and R' are each independently the same or different hydrocarbyl groups. A hydrocarbyl group may be defined as having a carbon atom directly attached to the remainder of the molecule and having predominantly hydrocarbon character. Examples of hydrocarbyl groups include: (1) hydrocarbon substituents, that is, aliphatic (e.g., alkyl or alkenyl), alicyclic substituents (e.g., cycloalkyl, cycloalkenyl), and aromatic-, aliphatic-, and alicyclic-substituted aromatic substituents, as well as cyclic substituents wherein the ring is completed through another portion of the molecule (e.g., two substituents together form an alicyclic radical); (2) substituted hydrocarbon substituents, that is, substituents containing non-hydrocarbon groups which, in the context of this invention, do not alter the predominantly hydrocarbon substituent [e.g., halo (especially chloro and fluoro), hydroxy, alkoxy, mercapto, alkylmercapto, nitro, nitroso, and sulfoxy]; and (3) hetero substituents, that is, substituents which, while having a predominantly hydrocarbon character, in the context of this invention, contain other than carbon in a ring or chain otherwise composed of carbon atoms. Hetero-atoms include sulfur, oxygen, nitrogen, and encompass substituents as pyridyl, furyl, thienyl and imidazolyl groups. In general, no more than two (preferably no more than one) non-hydrocarbon substituent will be present for every ten carbon atoms in the hydrocarbyl group; typically, there will be no non-hydrocarbon substituents in the hydrocarbyl group. Thus, examples of organic anhydrides that may be employed for practicing the current invention include those anhydrides which yield organic acids having between one and sixteen carbon atoms per molecule upon hydrolysis. As such, acetic anhydride, succinic anhydride, maleic anhydride, and phthalic anhydride are exemplary. Other anhydrides that may be employed are, without limitation, proprionic anhydride and methyl phthalic anhydride. Any mixture of anhydrides may also be employed. One preferred embodiment of the invention incorporates an anhydride that has a ring structure; examples of such an anhydride are maleic anhydride and methyl phthalic anhydride.

Alternatively, instead of employing anhydrides to produce the "organic linker group" of the inventive composition, acids, preferably carboxylic acids, may be linked to the polymer surface. For example, maleic acid can be conjugated to the polymer for this purpose.

Plasma may be used to treat polymer substrate surfaces in order to make the modifications necessary for practicing and preparing the current invention. Providing organic surface coatings on substrate materials by means of plasma deposition is a commonly used tool in the polymer arts and has been reviewed (Yasuda, 1976; incorporated by reference herein in its entirety). According to Yasuda, plasma-created by electric glow discharges contain a variety of organic species which are chemically active or energetic enough to cause the chemical reactions leading to covalent bonding of the organic species to a suitable polymer material. Protocols for generating plasmas and treating polymer surfaces therewith are widely known in the art; such methodology is disclosed in U.S. Pat. No. 5,364,662 to Domenico et al., which is herein incorporated by reference in its entirety. Other plasma reaction protocols have been developed (Gaboury and Urban, 1993; Gaboury and Urban, 1994; Zhao and Urban, 1999, which herein is incorporated by reference in its entirety). In one preferred embodiment of the present invention, anhydride such as maleic anhydride is converted into a plasma form using microwaves and consequently reacted with polymer; this process covalently links the anhydride to the polymer backbone. As such, polymer "surface-linked anhydride groups" are formed. Optionally, other means for generating plasma may be employed; for example, use of radio frequency microwaves is widely known in the art for this purpose.

Typically, when an anhydride is used to prepare the inventive composition (preparation of organic linker group), or when it is used in the inventive method, it is hydrolyzed after being covalently attached to a selected polymer. Such hydrolysis yields two carboxylic acid groups (i.e. dicarboxylic acid) that are useful for downstream attachment of polyalkylene glycol spacer molecules via optional esterification reactions. Such acid groups are considered to be polymer "surface-linked acid groups". Methods such as but not limited by simple boiling in water are well known in the art for performing anhydride hydrolysis.

In practicing the inventive method, one may directly choose to react the polymer surface-linked acid groups with polyalkylene glycol spacer molecules (such as by esterification) without further modification. If dicarboxylic acid groups are used, one may optionally choose to convert them to acid halide groups, thus forming polymer "surface-linked acid halide groups", prior to creation of ester groups. Any so formed acid halide of a carboxylic acid (including aryl and acyl halides) is suitable for use in practicing the current invention. An acid halide has the structure:

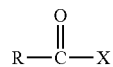

in which X is a halogen atom selected from fluorine (F), chlorine (Cl), bromine (Br), and iodine (I); and in which R is a hydrocarbyl group.

Acid halides are well known in the art, and are described in organic chemistry textbooks, such as that authored by Streitweiser and Heathcock (1981). Acid halides are the reaction product between a carboxylic acid and a suitable halogenating agent such as the trichloride and pentabromide of phosphorous, or the thionyl halides such as thionyl chloride and thionyl bromide. Acid halides can be hydrolyzed in a spontaneous reaction with water to form the corresponding carboxylic acid and a hydrohalic acid, as is well-known in the art.

In the formation of acid halides, the hydroxy group of a carboxylic acid group is replaced by a halogen atom, usually chlorine or bromine. Accordingly, for purposes of the instant application, the words "acid halide group" means the reaction product of a carboxylic acid having at least one carboxyl function with a halogenating agent, including, but not limited to phosphorous pentachloride or thionyl chloride, such that the hydroxy group of the carboxylic acid function of a carboxylic carbon atom is replaced by a halogen atom, such as a chlorine atom. These and other halogenating agents like N-bromo succinimide are known to those skilled in the art, and for purposes of this application a halogenating agent means a molecule which is capable of providing a halogen atom which can be incorporated into other different molecules, as in the case of the formation of acid halides. Acid halides yield a carboxylic acid and a hydrogen halide upon hydrolysis.

In practicing the present invention, the following non-limiting types of reactions (numbered 1-13) can be employed to link polyalkylene spacers (e.g. PEG) to the polymer surface-attached organic linker group (e.g. maleic anhydride or hydrolyzed maleic anhydride) and/or bio-active agents (e.g. antibiotic agent) to polymer surface-linked polyalkylene spacers. Some of these reactions are discussed in the above text as well as in the Examples. Skilled artisans would recognize that the provision of these reactions depends on the nature of the chemical components used for each organic linker, polyalkylene spacer and bio-active agent. For example, an amidation reaction (reactions 8-13) would likely be used to link gentamicin to the polyalkylene linker, since it is an aminoglycoside antibiotic with several amine groups but no carboxylic acid groups. Following from this thought, skilled artisans would know that, if gentamicin is the desired bio-active agent for polymer modification, an appropriate functionalized polyalkylene glycol spacer would be employed to provide, for example, a carboxylic acid group for nucleophilic attack by an amine group of gentamicin.

1. Alcohol+Carboxylic Acid

This condensation reaction yields an ester bond when performed at room temperature to about 250° C., more typically from 70 to 200° C., and most preferably from 90-150° C. While not necessary, the reaction can be run in the presence of a catalyst, such as hydrochloric acid or sulfuric acid. A coupling agent such as a carbodiimide can also be used to facilitate the attachment of the alcohol and acid at lower temperature. The water of esterification can also be removed from the reaction mixture in order to drive the reaction to higher conversion. This reaction is applicable, for example, for linking polyalkylene glycol (e.g. PEG) to surface linked acid groups.

2. Alcohol+Acid Halide

This condensation reaction yields an ester bond when performed at room temperature to about 230° C., more typically from 50 to 170° C., and most preferably from 70-120° C. While not necessary, this reaction may be run in the presence of a catalyst, such as hydrochloric acid or sulfuric acid. The byproduct from condensation can also be removed from the reaction mixture in order to drive the reaction to higher conversion. In considering reactions 1 and 2 together, skilled artisans would recognize that reaction 1 is often performed using reaction 2 as an intermediary step (i.e. carboxylic acid is first converted to an acid halide, which is then reacted with alcohol for ester group formation). Therefore, it should be understood that the reaction steps of the inventive method that can involve ester formation (e.g. "reacting the polymer surface-linked carboxylic acid groups with polyalkylene glycol") can incorporate the intermediary step of first creating an acid halide group from the carboxylic acid, followed then by ester formation between a glycol hydroxyl group and the acid halide group.

3. Alcohol+Acid Anhydride

This condensation reaction yields an ester bond when performed at room temperature to about 230° C., more typically from 70 to 200° C., and most preferably from 80-150° C. While not necessary, this reaction may be run in the presence of a catalyst, such as hydrochloric acid or sulfuric acid. The byproduct of esterification can also be removed from the reaction mixture in order to drive the reaction to higher conversion. Such a reaction can be used, for example, to link a surface-linked acid anhydride group (not hydrolyzed) of the organic linker with a hydroxyl group of a polyalkylene glycol spacer group. Also for example, this reaction can be used to link a hydroxyl group of a bio-active agent with an acid anhydride group of a surface-linked functionalized polyalkylene glycol spacer group.

4. Alcohol+Acid Salts

This condensation reaction yields an ester bond when performed at room temperature to about 250° C., more typically from 70 to 200° C., and most preferably from 80-150° C. While not necessary, this reaction may be run in the presence of a catalyst, such as hydrochloric acid or sulfuric acid. The byproduct of esterification can also be removed from the reaction mixture in order to drive the reaction to higher conversion. Such a reaction can be used, for example, to link a surface-linked carboxylic acid salt of the organic linker with a hydroxyl group of a polyalkylene glycol spacer group. Also for example, this reaction can be used to link a carboxylic acid salt of a bio-active agent with a hydroxyl group of a surface-linked polyalkylene glycol spacer group.

5. Alcohol+Isocyanate

This addition reaction yields a urethane bond when performed at room temperature. Catalyst can be added if needed to improve the reaction rate. The system should be kept free of water to avoid side reactions with the isocyanate.

6. Alcohol+Ester

This transesterification reaction yields a new ester bond when performed at room temperature to about 250° C., more typically from 110 to 220° C., and most preferably from 150-200° C. While not necessary, this reaction may be run in the presence of a catalyst, such as hydrochloric acid or sulfuric acid. The byproduct of transesterification can also be removed from the reaction mixture in order to drive the reaction to higher conversion. Such a reaction can be used, for example, to link a surface-linked ester group of the organic linker with a hydroxyl group of a polyalkylene glycol spacer group. Also for example, this reaction can be used to link a hydroxyl group of a bio-active agent with an ester group of a surface-linked functionalized polyalkylene glycol spacer group.

7. Two Carboxylic Acids

This dehydration can be catalyzed using a variety of commercially available catalysts and/or the temperature should be raised to a temperature to allow for dehydration depending on the composition of the two acids. Such a reaction can be used, for example, to link a surface-linked carboxylic acid of the organic linker with a carboxylic acid group of a functionalized polyalkylene glycol spacer group. Also for example, this reaction can be used to link a carboxylic acid group of a bio-active agent with a carboxylic acid group of a surface-linked functionalized polyalkylene glycol spacer group.

8. Amine+Isocyanate

This addition reaction yields a urea bond when performed at room temperature or higher temperatures. Catalyst can be added if needed to improve the reaction rate. The system should be kept free of water to avoid side reactions with the isocyanate.

9. Amine+Carboxylic Acid

This neutralization and dehydration reaction yields an amide bond (process also called amidation; amidation also occurs for reactions 10-13 below). When the amine and carboxylic acid react upon mixing, the acid-base neutralization forms ammonium carboxylate salts which can then be heated, for example, to greater than about 200° C. to dehydrate and form the amide bond. This reaction is applicable, for example, for linking functionalized polyalkylene glycol (e.g. PEG with an amine terminus) to surface linked acid groups.

10. Amine+Acid Halide

This substitution reaction yields an amide bond. The primary and secondary amines can react at low temperatures by nucleophilic acyl substitution to form amides generally in a mixed solvent system with water and an organic solvent. In considering reactions 9 and 10 together, skilled artisans would recognize that reaction 9 is often performed using reaction 10 as an intermediary step (i.e. carboxylic acid is first converted to an acid halide, which is then reacted with an amine for amide group formation). Therefore, it should be understood that the reaction steps of the inventive method that can involve amide formation (e.g. "reacting the polymer surface-linked carboxylic acid groups with polyalkylene glycol or functionalized polyethylene glycol (PEG)", where the functionalized PEG has an amine terminus) can incorporate the intermediary step of first creating an acid halide group from the carboxylic acid, followed then by amide formation between an amine group of a functionalized polyalkylene glycol spacer and the acid halide group.

11. Amine+Acid Anhydride

This substitution reaction yields an amide bond. The primary and secondary amines can react at low temperatures by nucleophilic acyl substitution to form amides generally in a mixed solvent system with water and an organic solvent. Such a reaction can be used, for example, to link a surface-linked acid anhydride group of the organic linker with an amine group of a functionalized polyalkylene glycol spacer group. Also for example, this reaction can be used to link an amine group of a bio-active agent with an acid anhydride group of a surface-linked, functionalized polyalkylene glycol spacer group.

12. Amine+Acid Salts

This reaction yields an amide bond. The amine and acid salts react through acid-base neutralization to form ammonium carboxylate salts which can be heated, for example, to greater than about 200° C. to dehydrate and form the amide bond. Such a reaction can be used, for example, to link a surface-linked carboxylic acid salt group of the organic linker with an amine group of a functionalized polyalkylene glycol spacer group. Also for example, this reaction can be used to link an amine group of a bio-active agent with a carboxylic acid salt group of a surface-linked, functionalized polyalkylene glycol spacer group.

13. Amine+Ester

This reaction yields an amide bond and may require, for example, heating to from 50 to 250° C., and more preferably from 100 to 200° C. to form the bond. Such a reaction can be used, for example, to link a surface-linked ester group of the organic linker with an amine group of a functionalized polyalkylene glycol spacer group. Also for example, this reaction can be used to link an amine group of a bio-active agent with an ester group of a surface-linked, functionalized polyalkylene glycol spacer group.

Practitioners of the current invention can preferably choose to attach polyalkylene glycol spacer molecules to the polymer surface-attached acid groups, whether they be carboxylic acid or acid halide groups, via esterification or amidation. By doing so, at least two ester groups or amide groups will be formed in the organic linker group (if, for example, an anhydride or dicarboxylic acid was first used to modify the polymer surface). The attachment of polyalkylene glycol spacers, or their equivalent (e.g. functionalized PEG spacers), is an important feature of the current invention, as it provides a flexible polymer surface that is better able to present further attached antibiotic molecules, or other bio-active agents. Further, the provision of two or more polyalkylene glycol spacer molecules of different molecular weight will provide uneven contour to the polymer surface; such provides more surface area and thus gives any attached antibiotic molecules greater exposure to the external environment. Though the application should not be held to any particular theory, this feature may provide the invention with enhanced antimicrobial activity. Particular embodiments of the invention incorporate PEG as the polyalkylene. One such embodiment incorporates PEG 200 and PEG 600; however, a range of molecular weights of PEG may also be used. Preferably, the molecular weight range of incorporated PEG is between 100 and 2000, or more preferably from 100 and 800. Preferably, by virtue of using two or more different molecular weight forms, linear PEG spacers of different lengths will be incorporated on the polymer surface. These preferred molecular weights and mixtures also apply to functionalized PEG forms that can be incorporated in the invention (refer below).

PEG has the Following Formula:

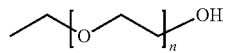

Skilled artisans would readily be able to estimate the number of ethylene oxide monomers (given as n in above formula) that are in any given molecular weight species of PEG. Since the shorthand formula for PEG is $C_{2n}H_{4n+2}O_{n+1}$, one may easily determine n value of PEG is the molecular weight thereof is known, and vice versa.

Polyalkylene glycols are well known in the art. Polyalkylene glycols that can be incorporated in the current invention include, but not limited to, polyalkylene glycol homopolymers, polyethylene/polypropylene glycol copolymers, polyethylene/polypropylene diol copolymers, polyglycerins, and mixtures thereof, and/or their derivatives, and/or mixtures thereof. Polyalkylene glyceryl ethers may also be employed.

Further, polyalkylene glycol may comprise for purposes of the present invention PEG, a polypropylene glycol and/or alkoxy polyethylene/polypropylene glycol copolymer. Specific examples of suitable polyalkylene glycol polymers include: polyethylene/polypropylene glycol copolymers (e.g., methoxy, ethoxy, propoxy, butoxy, and pentoxy polyethylene/polypropylene glycols), triglycerin, hexaglycerin, PPG-4, PPG-6, PEG-5, PEG-6, PEG-8, PEG-12, PEG-14, PEG-18, and mixtures thereof. Various forms and equivalents of PEG, such as those disclosed in U.S. Pat. No. 7,208,145 (herein incorporated by reference in its entirety), may employed in the current invention.

Any polyalkylene glycol, or any equivalent thereof, used in the current invention should preferably contain a terminal hydroxyl group in order to permit its esterification to the acid (e.g. carboxylic or acid halide) of the organic linker group. Appropriate equivalents of polyalkylene glycol are well known in the art. Although a hydroxyl group on the polyalkylene glycol is preferred, functionalized polyalkylene glycol (e.g. functionalized PEG) may be employed instead of polyalkylene glycol species that terminate with hydroxyl groups. A preferred functionalized PEG for use in the present invention has the formula:

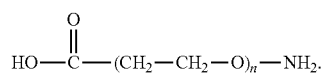

This functionalized form of PEG can be written in shorthand as COOH—PEG-NH$_2$. Thus, functionalized polyalkylene glycol species such as functionalized PEG have a functional group besides a hydroxyl group on at least one terminus. Skilled artisans would recognize, especially in view of the present disclosure, that the current invention is amenable to the provision of a variety of functionalized polyalkylene species. The following are additional non-limiting examples of functionalized PEG (in shorthand): NH$_2$—PEG-NH$_2$, NH$_2$—PEG-COOH, COOH—PEG-COOH, OH—PEG-COOH, COOH—PEG-OH, OH—PEG-NH$_2$ and NH$_2$—PEG-OH. Written further in shorthand, functionalized PEG can be represented as X—PEG-Y, where X and Y can individually be, for example, NR$_1$R$_2$ (i.e. primary, secondary or tertiary amine), ketimine (primary or secondary), aldimine (primary or secondary), imide, azide, azo, cyanate, isocyanide, isocyanate, isothiocyanate, nitrate, nitrile, nitrosooxy, nitro, nitroso, pyridyl, COOH (carboxylic acid), OH (hydroxyl), SH (thiol), COOR$_1$ (ester), anhydride, acyl halide, carbonyl, aldehyde, carbonate ester, ether, hydroperoxy, peroxy, carboxamide, phosphate, phosphino, phosphono, sulfo, sulfinyl, sulfonyl, and disulfide groups. R$_1$ and R$_2$ may be hydrogen or any organic group (i.e. mostly carbon and hydrogen, but may also have oxygen and nitrogen). Other forms of functionalized PEG used in the invention can be monoglycidyl (e.g. glycidyl-PEG-OH) or diglycidyl PEG, the latter of which has the formula:

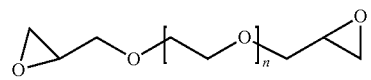

In practicing the present invention, skilled artisans would understand that the provision of certain functional groups on the chosen polyalkylene spacer would necessitate the use of certain other complementary functional groups on the surface-linked organic group and the bio-active group. Complementary functional groups are largely those that will engage in a condensation reaction, thereby forming a linkage.

An antibiotic agent, which is an example of a bio-active agent, is incorporated in the current invention and is linked to the polyalkylene spacer so that the antibiotic is exposed to the external environment (i.e., the antibiotic is not sandwiched or hidden beneath the polyalkylene spacer and organic linker groups). Specifically, the antibiotic agent is linked to the terminus of the polyalkylene spacer molecule that is not in ester linkage to the organic linker. Preferably, the antibiotic agent is in ester linkage with the polyalkylene spacer. It is the surface modification of a polymer with antibiotics that renders the polymer surface as antimicrobial.

Several antibiotic agents can be incorporated in the present invention and include, for example, penicillins (e.g. amoxicillin), cephalosporins, vancomycins, aminoglycosides, quinolones, polymyxins, erythromycins, tetracyclines, chloramphenicols, clindamycins, lincomycins, sulfonamides, and analogs, derivatives, pharmaceutical salts and mixtures thereof. The aforementioned agents tend to be anti-bacterial and anti-fungal in nature. Penicillins are an example of antibiotic agents incorporating a β-lactam ring; a well known specific example thereof is ampicillin. Gentamicin is a well known aminoglycoside antibiotic.

The present invention may optionally incorporate antibiotic agents that exhibit toxicity towards mammalian cells and therefore may be useful for targeting cancer cells or any other cell population exhibiting undesired growth and/or physiologic activity. Examples of such agents are paclitaxel, docetaxel, alkylating agents including mechlorethamine, chlorambucil, cyclophosphamide, melphalan and ifosfamide; antimetabolites including methotrexate, 6-mercaptopurine, 5-fluorouracil and cytarabine; plant alkaloids including vinblastine, vincristine and etoposide; antibiotics including doxorubicin, daunomycin, bleomycin, and mitomycin; nitrosureas including carmustine and lomustine; inorganic ions including cisplatin; and analogs, derivatives, pharmaceutical salts and mixtures thereof.

The present invention may optionally incorporate antibiotic agents that have antiviral activity, including, for example, amantadines, rimantadines, ribavirins, idoxuridines, vidarabines, trifluridines, acyclovirs, gancicloviES, zidovudines, foscamets, and analogs, derivatives, pharmaceutical salts and mixtures thereof.

The present invention may optionally incorporate other bio-active agents (i.e. functional groups) beside antibiotic agents. For example, the following non-steroidal anti-inflammatory drugs that incorporate a carboxylic acid group can be linked to polymers modified by the present invention: aspirin, diflunisal, diclofenac, aceclofenac, acemetacin, etodolac, indometacin, sulindac, tolmetin, ibuprofen, carprofen, fenbufen, fenoprofen, flurbiprofen, ketoprofen, ketorolac, loxoprofen, naproxen, oxaprozin, tiaprofenic acid, suprofen, mefenamic acid, meclofenamic acid and lumiracoxib. Also for example, the following non-steroidal anti-inflammatory drugs that incorporate a hydroxyl group can be linked to polymers modified by the present invention: oxyphenbutazone, piroxicam, lornoxicam, meloxicam and tenoxicam. And as yet another example, the following steroidal anti-inflammatory drugs that incorporate a hydroxyl group can be linked to polymers modified by the present invention: hydrocortisone, prednisone, prednisolone, methylprednisolone, dexamethasone, betamethasone, triamcinolone, beclometasone, fludrocortisone acetate and aldosterone.

In another example, the present invention may incorporate the following chemotherapetuic agents as the bio-active agent (the parenthetical expression following each agent refers to the chemical group comprised in the agent that could be exploited for attachment reactions): melphalan (amine/acid), chlorambucil (acid), dacarbazine (amine), temozolomide (amine), streptozotocin (hydroxyl), methotrexate (acid/amine), pemetrexed (acid/amine), raltitrexed (acid), tioguanine (amine), fludarabine (amine/hydroxyl), pentostatin (hydroxyl), cladribine (amine/hydroxyl), floxuridine (hydroxyl), gemcitabine (amine/hydroxyl), vincristine (hydroxyl), vinblastine (hydroxyl), vinorelbine (hydroxyl), vindesine (hydroxyl/amine), etoposide (hydroxyl), teniposide (hydroxyl), irinotecan (hydroxyl), topotecan (hydroxyl), paclitaxel (hydroxyl), docetaxel (hydroxyl), warfarin (hydroxyl), acenocoumarol (hydroxyl), phenprocoumon (hydroxyl), argatroban (acid/amine) and ximelagatran (amine). The term "acid", as listed parenthetically as a chemical group in certain of the above chemotherapeutic agents, refers to a carboxylic acid group.

The following schematics represent examples of compositions that can result from practicing the inventive method. In these schematics, "PEG" represents repeating (O—CH$_2$—CH$_2$) units. For additional examples, consult FIGS. 1 and 9.

Schematic 1:

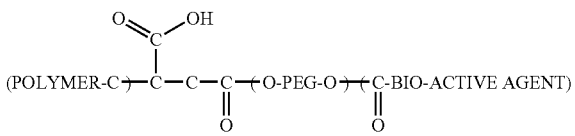

Schematic 2:

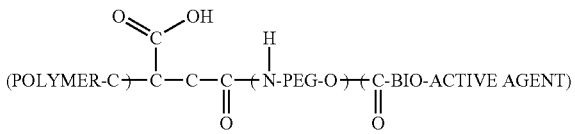

Schematic 3:

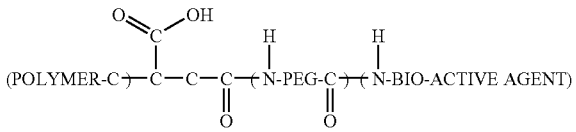

Schematic 4:

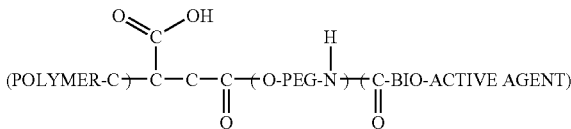

The current invention may be used to devise medical devices, such as implanted medical devices and devices that perform ex vivo functions (e.g. dialysis machine), that are resistant to bacterial colonization (i.e. biofilms will not develop thereupon). Examples of such devices include a variety of vascular catheters such as peripherally insertable central venous catheters, dialysis catheters, long term tunneled central venous catheters, peripheral venous catheters, single-lumen and multiple-lumen short-term central venous catheters, arterial catheters and pulmonary artery Swan-Ganz catheters, urinary catheters, other long-term urinary devices, tissue bonding urinary devices, penile prostheses, vascular grafts, vascular catheter ports, wound drain tubes, hydrocephalus shunts, peritoneal dialysis catheters pacemaker capsules, artificial urinary sphincters, joint replacements, urinary dilators, heart valves, artificial hearts, stents, prostheses, cochlear implants, artificial corneas, contact lenses, silicone implants, dental implants, surgical tapes and sutures, and colostomy bags.

The current invention may also be used to devise industrial components that are less prone to biofilm growth thereupon (i.e. for anti-fouling purposes). Examples of such components include pipes, spigots, air ventilation systems, and fermentors. Skilled artisans would recognize that present invention lends itself to modifying polymer surfaces for reasons besides forming an antimicrobial surface. For example, an anti-inflammatory agent, such as one listed above, may be attached to an implanted device to control undesirable swelling reactions.

The following examples are included to demonstrate certain preferred embodiments of the invention for extra guidance purposes. As such, these examples should not be construed to limit the invention in any manner.

EXAMPLES

Example 1

Generating Acid Groups on the Surface of ePTFE Polymer

FIG. 1 illustrates a strategy for performing surface reactions that are amenable for producing antimicrobial ePTFE surfaces. An effective method of generating acid groups on polymeric surfaces is the employment of surface microwave plasma reactions in the presence of maleic anhydride, followed by surface hydrolysis thereof (Gaboury and Urban, 1993). These reactions are illustrated in FIG. 1 (steps 1 and 2). The generation of carboxylic acid (COOH) groups on the ePTFE surface is useful because of their functionality with regards to carrying out further surface modifications.

The following protocol was carried out to generate acid groups on the surface of ePTFE. ePTFE specimens were purchased from Philips Sci Inc. (Rock Hill, S.C.), cut to 7×7 mm squares, followed by washing with acetone in an ultrasonic washer, and dried at room temperature under vacuum conditions before use. Plasma reactions were conducted using open reactor conditions, as described elsewhere (Gaboury and Urban, 1993, herein incorporated by reference in its entirety). The ePTFE substrate and 100 mg of solid maleic anhydride (Aldrich Chemical Co.) were placed into a microwave reactor chamber and spaced 8.5 cm apart from each other. In a typical experiment, the reactor was evacuated to 150 mTorr, followed by purging it with argon (Ar) gas to reach a steady state pressure of 250 mTorr at a flow rate of 2.96 mL/min. Once these environmental conditions were established, microwave radiation at 600 W of power with an output frequency of 2.45 GHz was activated to induce plasma formation (FIG. 1, step 1). Under these conditions, the reaction chamber pressure increases continuously during the microwave plasma discharge. In an effort to maintain a plasma environment to permit longer exposure times, a vacuum was applied continuously to maintain pressure conditions during the experiment. Since monomeric and polymeric forms of MA are water soluble, the samples were boiled in water for 30 min (FIG. 1, step 2) in an effort to determine stability of the surface treatments and to ensure that the newly formed species are not physisorbed on the ePTFE surface. After drying, specimens were stored in a desiccator under ambient conditions.

Figure 3:
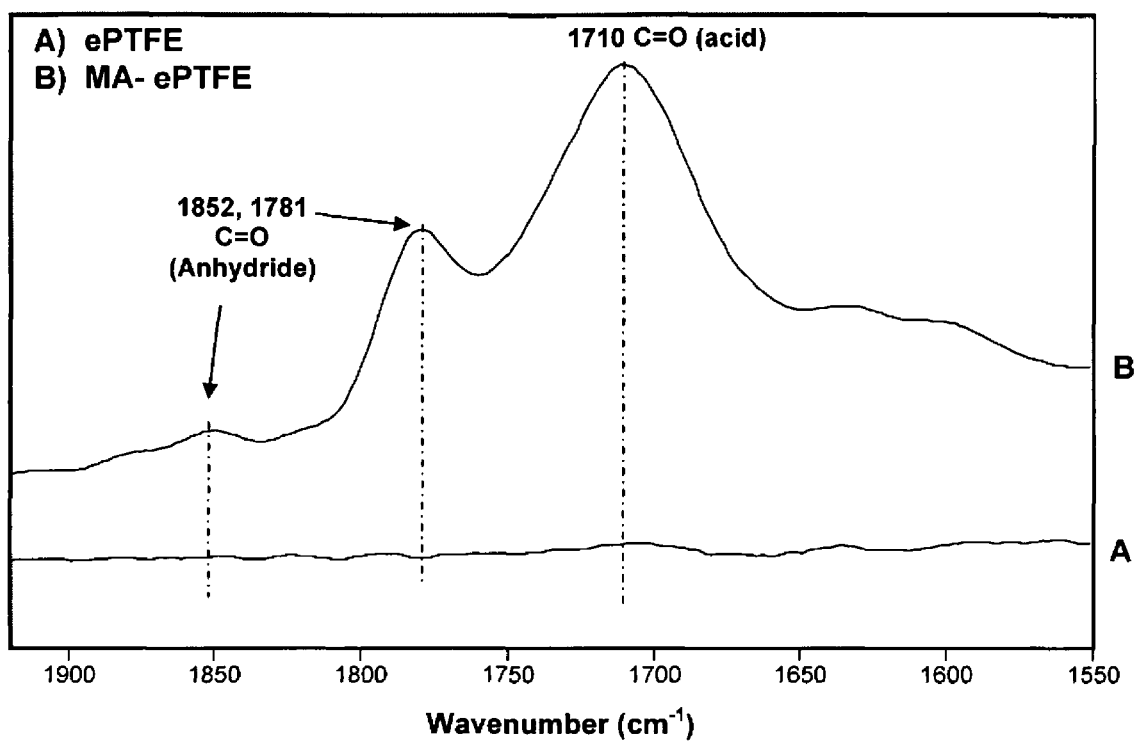
FIG. 3: Attenuated total reflectance Fourier transform infrared (ATR-FTIR) spectra of: A) ePTFE, and B) MA/ePTFE.

In an effort to confirm that these reactions did in fact occur on the ePTFE surface, analysis was performed thereupon. FIG. 3 illustrates attenuated total reflectance Fourier transform infrared (ATR-FTIR) spectra recorded from the surface of ePTFE before (trace A) and after (trace B) the above-described plasma and hydrolysis reactions were performed. As expected, there are no bands in the 1900-1500 $cm^{-1}$ region for unmodified ePTFE (trace A). In contrast, as illustrated in trace B of FIG. 3, the bands at 1781, 1852 and 1710 $cm^{-1}$ are detected as a result of the microwave plasma reactions. These bands are attributed to anhydride C=O and acid C=O stretching vibrations (Pretsch et al., 2000; Colthup et al., 1975; Bellamy, 1975); these data indicate that the ePTFE polymer surfaces were chemically modified via opening of the maleic anhydride C=C bond and the consequent hydrolysis of the anhydride group (Gaboury and Urban, 1993).

Figure 4:
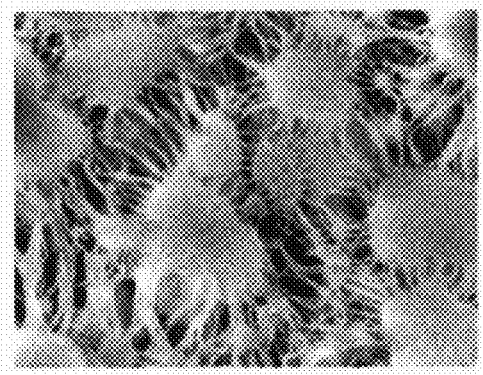
FIG. 4: Scanning electron microscope (SEM) images of: A) ePTFE, B) plasma-reacted ePTFE, and C) plasma-reacted ePTFE in the presence of MA.
Figure 4:
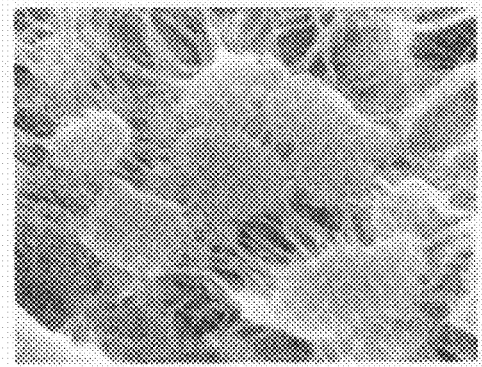
Figure 4:
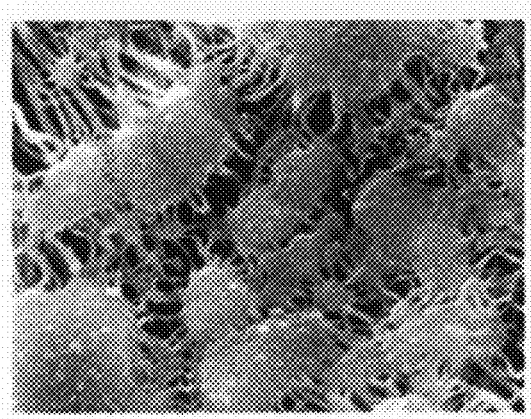

One of the significant differences between PTFE and ePTFE polymers is surface morphology. As shown in FIG. 4A, a scanning electron microscope (SEM) image of ePTFE shows a mesh-like network morphology; this morphology is highly functional in bio-environments as it provides architecture that is conducive for growth of body tissue on and within the artificial network. As shown in the SEM images of FIG. 4, as a result of microwave plasma surface reactions without (B) and in the presence of maleic anhydride (C), the ePTFE surface morphology remains virtually the same; the only difference is the formation of whitish particle-like sparkles. However, ATR-FITR measurements illustrated in FIG. 3 clearly show that carboxylic acid (COOH) modifications have occurred. It should also be noted that these reactions result in a water contact angle change from 125° for ePTFE to 95° for COOH-modified ePTFE. To date, modification of ePTFE using the above-described process has not previously been performed.

The above-described SEM and ATR-FITR analyses were performed according to the following parameters. A scanning electron microscope Quanta FEI series 200 FEG was used to evaluate polymer surface morphologies. All specimens were sputter-coated with gold and analyzed at a 45° angle with a scanning electron beam. ATR FTIR spectra were collected using a Bio-Rad FTS-6000 FTIR single-beam spectrometer set at a 4 $cm^{-1}$ resolution equipped with a deuterated triglycine sulfate (DTGS) detector and a 45° face angle Ge crystal. Each spectrum represents four-hundred co-added scans normalized against a reference spectrum obtained by recording four-hundred co-added scans of an empty ATR cell. All spectra were corrected for spectral distortion using Q-ATR software (Urban, 1996).

Example 2

Producing an Antimicrobial Surface on ePTFE Polymer that has been Pre-Modified with Acid Groups Penicillin (PEN) was chosen as the antibiotic for modifying ePTFE polymer to create an antimicrobial surface, whereupon bacterial colonization and biofilm formation is prevented. To this end, it may be preferable to provide suitable surface functionality and morphology to the ePTFE polymer in order to 1) affix penicillin thereupon and to 2) optimize bactericidal effects of PEN once affixed. Although acid groups are capable of reactions with PEN, the anti-bacterial activity of PEN when attached closely to the polymer surface may be compromised. Therefore, to enhance the anti-bacterial activity of surface-attached PEN, we introduced flexible spacer groups between the COOH-functionalized surface and PEN molecules. The choice of PEG was dictated by its non-toxicity, biocompatibility, and the ability to swell in aqueous environments (Levesque et al., 2002; Elbert and Hubbell, 1996; both incorporated by reference herein in their entirety). Additionally, in an effort to further enhance antimicrobial surface activity, a non-uniform surface morphology was prepared by employing various lengths of PEG spacers (i.e. PEG molecules of different molecular weight). The premise behind this morphological approach is that by introducing random esterification reactions between surface acid groups and hydroxyl (OH) groups of linear PEG of two or more molecular weights, molecular roughness is introduced to the surface, which is capable of enhancing antimicrobial functionality of any antibiotic such as PEN further attached to the PEG groups. In this example, PEG of 200 and 600 MW was employed. The enhanced surface roughness produced by this method employing varying PEG chain lengths increases the effective surface area that may come into contact with bacterial cells; therefore, more bacteria will be exposed to any antibiotic attached to the surface will. This concept is illustrated in FIG. 2, which schematically shows the surface attachment of PEG (A, note the surface contour rendered by the different MW PEG groups), followed by attachment reactions with PEN (B), and anticipated retardation of bacteria in contact with the modified surface (C).

The following protocol was carried out to attach PEG to the polymer surface as modified in Example 1 to contain acid groups. PEG (Aldrich) was used as a spacer between modified ePTFE surfaces and PEN (refer to above discussion). The COOH acid groups on ePTFE surfaces were first converted into acid chloride using thionyl chloride ($SOCl_2$) solvent under reflux conditions at 65° C. for six hours (FIG. 1, step 3). This conversion of the COOH groups to acid chloride functionalities creates more reactive groups for further downstream reactions with PEG hydroxyl groups. After the reaction, a sample was removed from the flask and washed with chloroform to eliminate excess thionyl chloride. The acid chloride ePTFE surfaces were then placed into a chloroform solution of PEG containing a 1:1 molar ratio of linear PEG 200 and 600 MW. This esterification reaction was then carried out in a sealed flask at room temperature for eighteen hours. A small amount (1-2 drops) of triethylamine was added into the reaction flask at the onset of the reaction to neutralize hydrochloric acid generated during the reaction (FIG. 1, step 4). After the incubation period, the sample was washed with chloroform several times to remove any excess non-reacted PEG, and then washed with distilled water for two hours (Wang et al., 2000).

Figure 5:
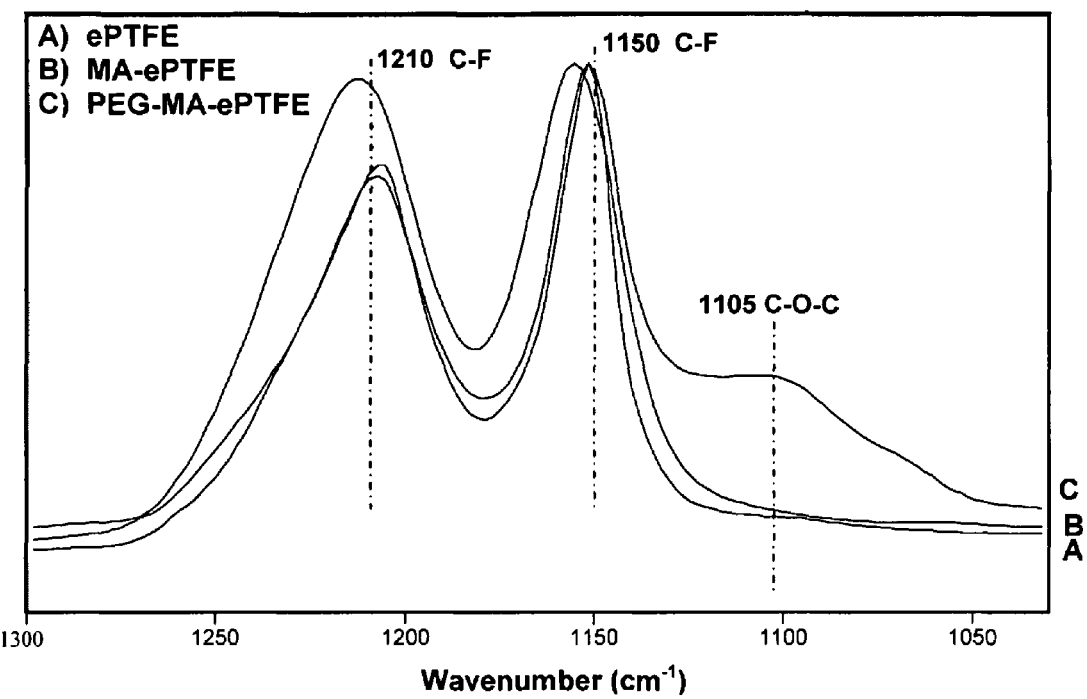
FIG. 5: ATR-FTIR spectra in the 1300-1000 cm$^{-1}$ (a) and 1900-1600 cm$^{-1}$ (b) regions of: A) ePTFE, B) MA-ePTFE, and C) PEG-MA-ePTFE. Refer to Example 2.
Figure 5:
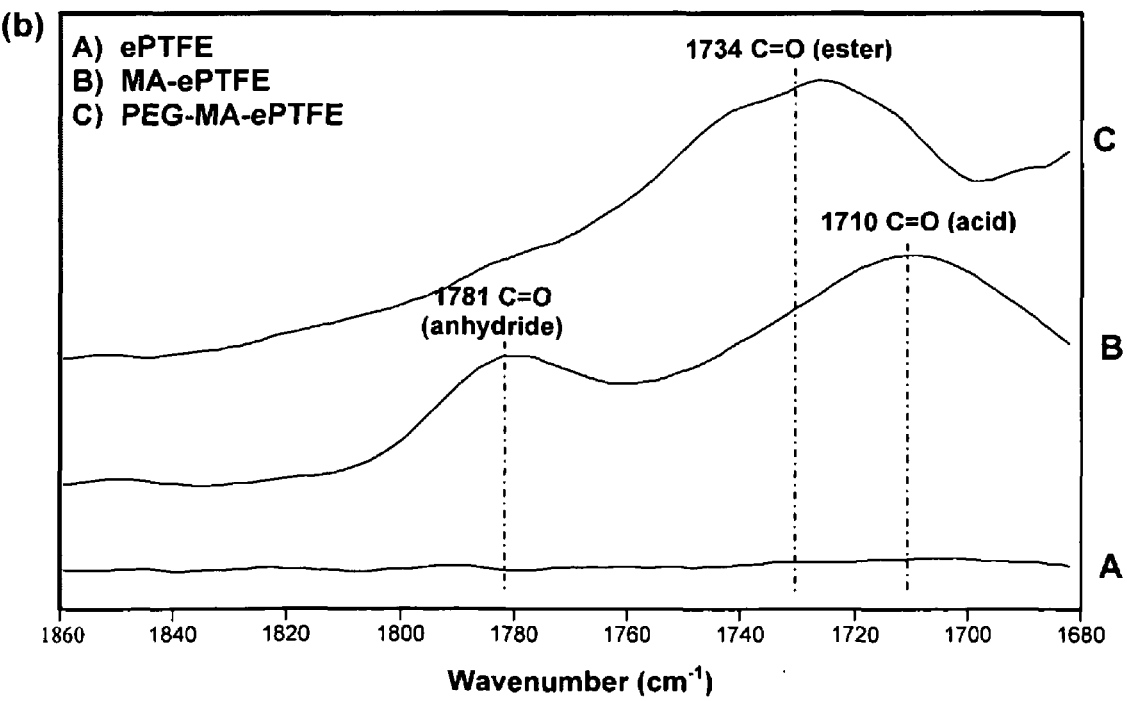
Figure 6:
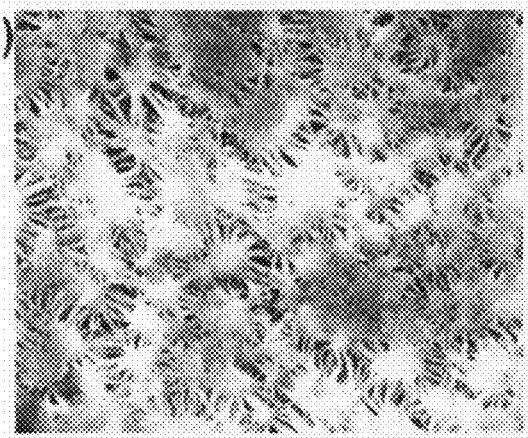
FIG. 6: SEM images of: A) ePTFE, B) MA-ePTFE and C) PEG-MA-ePTFE. Refer to Example 2.
Figure 6:
Figure 6:
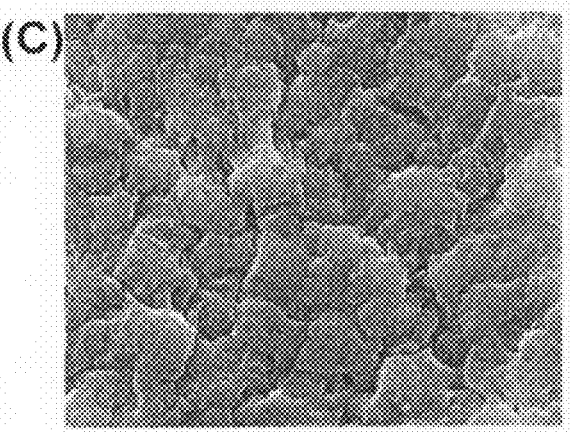

In a similar manner to the procedure described in Example 1, ATR-FTIR was utilized to determine the extent to which the surface reactions with PEG proceeded as intended. FIG. 5 (a and b) shows ATR-FTIR spectra of unmodified ePTFE (trace A), MA-ePTFE (trace B), and PEG-MA-ePTFE (trace C) in the 1300-1000 $cm^{-1}$ (a) and 1850-1680 $cm^{-1}$ (b) spectral regions. While traces A and B serve as references, trace C illustrates the presence of the 1105 and 1734 $cm^{-1}$ bands due to C—O—C stretching and C=O ester vibrations (Pretsch et al., 2000; Colthup et al., 1975; Bellamy, 1975) resulting from successful PEG esterification to the acid groups. These spectra were normalized to the C—C stretching vibrations at 1177 $cm^{-1}$. SEM images shown in FIG. 6 illustrate surface morphologies of unmodified ePTFE (A), MA-ePTFE (B), and PEG-MA-ePTFE (C); note that the ePTFE surface modified with PEG (FIG. 6C) is significantly altered as a result of the reactions and exhibits fewer voids. These SEM images provide visual evidence that the above-described strategy for enhancing the surface area of polymer surfaces with PEG was in fact successfully accomplished.

Figure 7:
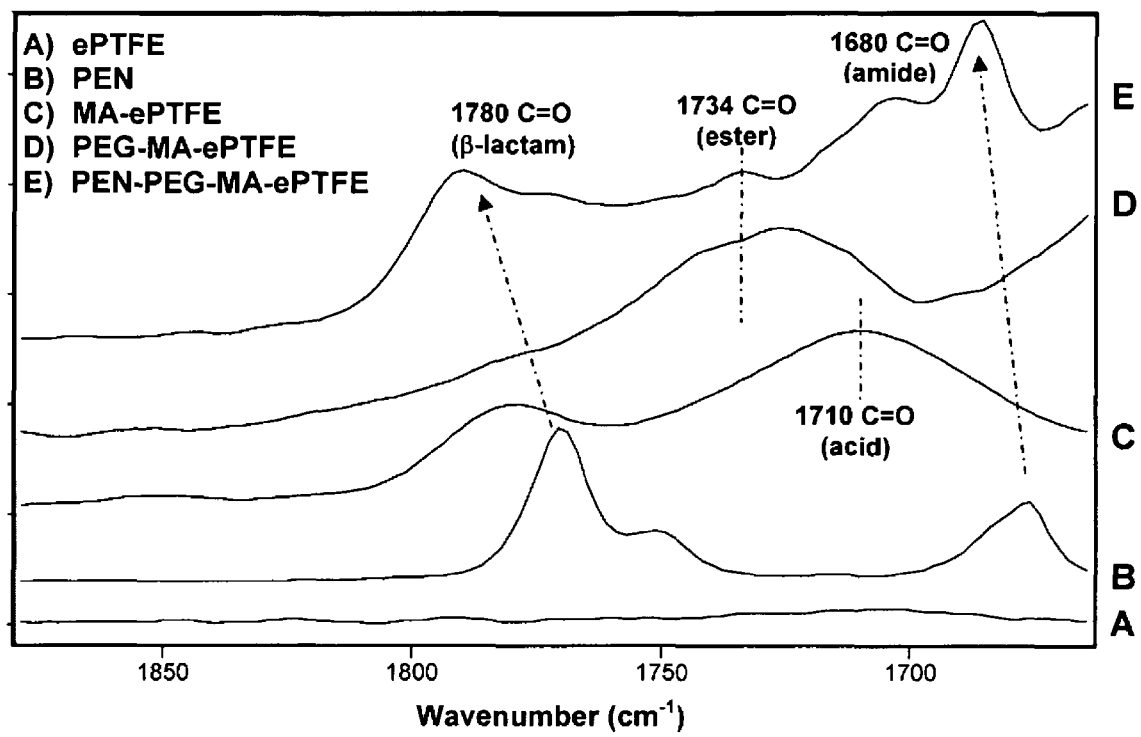
FIG. 7: ATR-FTIR spectra in the 1900-1650 cm$^{-1}$ region of: A) ePTFE, B) PEN, C) MA-ePTFE, D) PEG-MA-ePTFE, and E) PEN-PEG-MA-ePTFE. Refer to Example 2.

As illustrated in FIG. 1 (step 5), the final step for preparing an antimicrobial surface on ePTFE polymer involves reactions of PEG-MA-ePTFE with an antibiotic such as PEN. For that reason, esterification reactions were employed wherein dicyclohexyl-carbodiimide (DCC) was used as the coupling reagent and 4-(dimethylamino)-pyridine (DMAP) as the catalyst. These reactions can be carried out in one step process and do not require prior activation of the reactants. As a result of performing this reaction, PEN was attached to modified ePTFE surfaces via ester linkages. In order to demonstrate that this reaction did in fact occur, ATR-FTIR analysis was performed (FIG. 7). Again, for control reference purposes, traces A and B in FIG. 7 represent the spectra of ePTFE and PEN, respectively, while trace E represents the spectrum of PEN-PEG-MA-ePTFE. The presence of C=O vibrations is detected in trace E at 1680, 1734 and 1780 $cm^{-1}$, which are attributed to amide, ester, and β-lactam C=O stretching vibrations, respectively (Pretsch et al., 2000; Colthup et al., 1975; Bellamy, 1975), and indicates that the β-lactam ring of PEN remains intact during the esterification coupling reactions. This is an important note, since it is the β-lactam ring that gives PEN and certain related antibiotics their antimicrobial activity. In summary, these spectroscopic data illustrate that PEN was chemically attached to the ePTFE surface via linkage to the PEG extensions.

Figure 8:
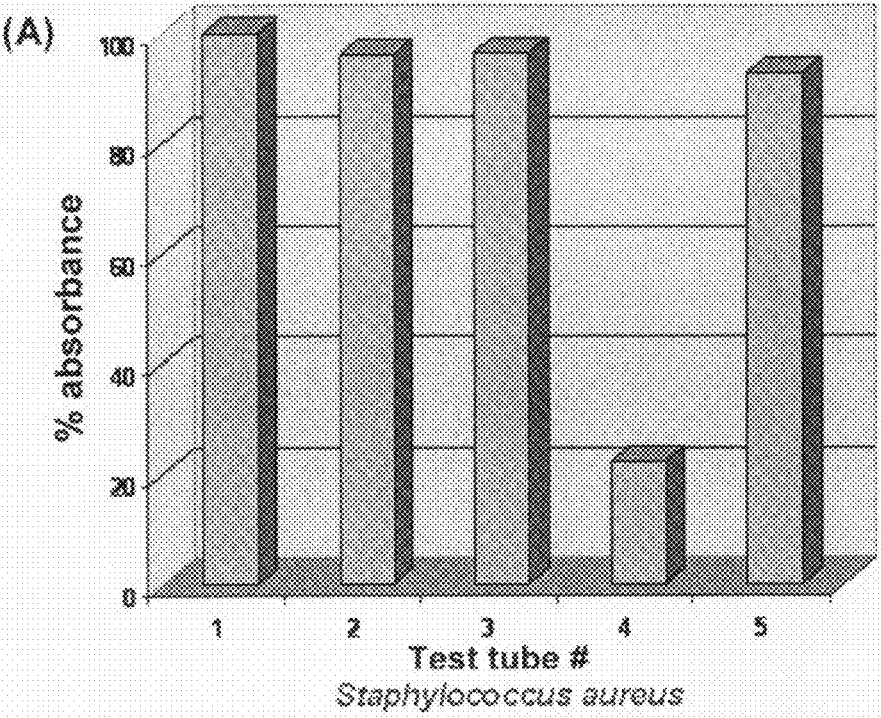
FIG. 8: Percent absorbance (600 nm) for liquid *Staphylococcus aureus* and *Pseudomonas aeruginosa* bacterial cultures grown in the presence of ePTFE (1), MA-ePTFE (2), PEG-MA-ePTFE (3), PEN-PEG-MA-ePTFE (4), and PEN-ePTFE (5). Refer to Example 3.
Figure 8:
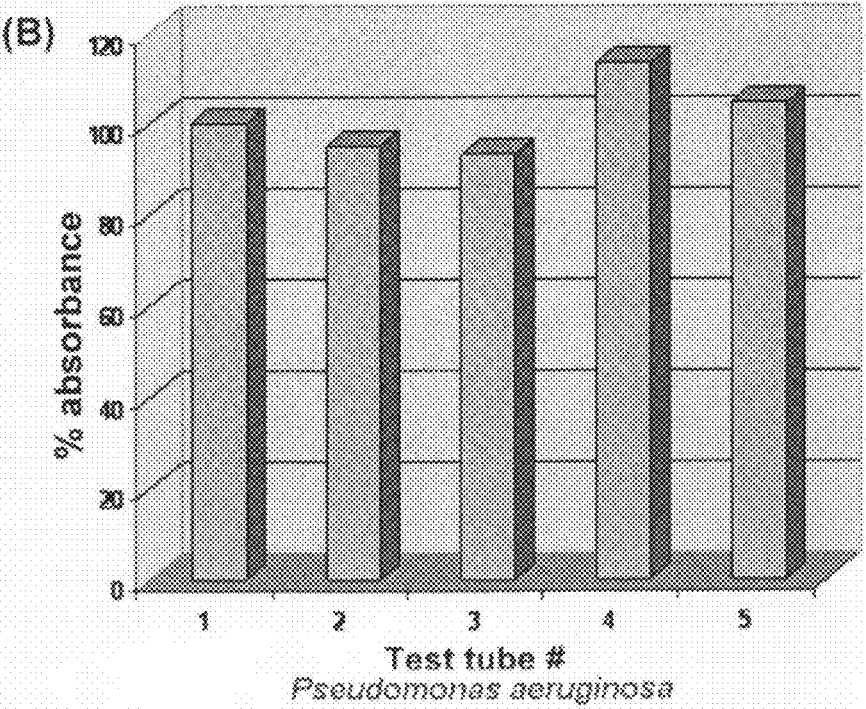

The following protocol was carried out to attach PEN to the PEG extensions on ePTFE polymer surfaces. In order to modify PEG-MA-ePTFE surfaces with PEN (Sigma Inc.), an esterification reaction using DMAP catalyst and DCC coupling agent was employed (Zalipsky et al., 1983; Yang and Lopina, 2003); refer to FIG. 1 (step 5). The K salt of penicillin V (PEN V) (1.5 mmol) was dissolved in a small volume of water, cooled, and acidified with 0.1 N HCl. Precipitated PEN V was filtered and dried in a vacuum oven at room temperature for one hour (Mole, 1992). PEG-MA-ePTFE specimens and DMAP (0.25 mmol) were placed into a 100-mL flask with 20 mL of methylene chloride. In the next step, dried PEN V was added to the mixture which was then stirred and cooled in an ice-water bath. DCC (1.3 mmol) was added and the mixture was continuously stirred for four hours. Upon removal, all specimens were washed in methylene chloride sequentially for two hours, dried for twenty-four hours, and analyzed by ATR-FTIR (FIG. 7, trace E) and for antimicrobial activity (FIG. 8, see below).

Example 3

Demonstrating the Antimicrobial Activity of ePTFE Polymer Surfaces Modified with Antibiotic In an effort to demonstrate the effectiveness of these surface reactions with respect to antimicrobial activity, a series of experiments was conducted in which modified and unmodified ePTFE specimens were placed into bacterial cultures. To carry out this analysis, *Staphylococcus aureus* (RN 6390) and *Pseudomonas aeruginosa* (ATCC, Rockville, Md.) were allowed to grow overnight in LB broth and King's medium, respectively. A series of specimens (ePTFE, MAePTFE, PEG-MA-ePTFE, PEN-PEG-MA-ePTFE, and PEN-ePTFE) were immersed into freshly incubated cultures of each bacteria and incubated at 37° C. for three to four hours. Anti-microbial activity was determined both by visual observation of the cultures as well as by measuring the absorbance of each culture at 600 nm using a UV-VIS spectrometer (Beckman DU-600).

Photographs (data not shown) were taken that depict turbidity differences in *Staphylococcus aureus* cultures as a result of exposure to ePTFE and modified forms thereof (culture data summarized in FIG. 8A). While test tubes #1, 2, and 3 represent three controls of bacteria growth in the presence of neat ePTFE, MA-ePTFE, and PEG-MA-ePTFE, respectively, test tube #4 shows a bacterial culture which included a PEN-PEG-MA-ePTFE specimen. Only the PEN-PEG-MA-ePTFE specimen was able to retard bacterial growth, as seen by the lack of turbidity in the growth medium (data not shown, see FIG. 8A). In contrast, the cloudiness of the solutions containing ePTFE, MA-ePTFE, and PEG-MA-ePTFE (test tubes #1, 2, and 3, respectively) indicates bacterial growth. A PEN-ePTFE specimen lacking PEG extensions was also tested on bacterial growth. Such a PEN-ePTFE specimen was prepared via an attempt to directly modify ePTFE with PEN only (i.e. steps 1-4 in FIG. 1 were skipped). As seen in a photograph (data not shown, see FIG. 8A), the solution in test tube #5 is turbid and supports bacterial growth. This result may indicate that the reaction of PEN to unmodified ePTFE surfaces did not occur, and by extension that otherwise unmodified ePTFE surfaces are not capable of retarding bacterial growth. Alternatively, this result may indicate that PEN-modified ePTFE surfaces that lack an intervening PEG layer are unable to adequately inhibit bacterial growth. Regardless, the failure of PEN-ePTFE to function as an antibacterial demonstrates the surprising effectiveness of employing PEG extensions in polymer surface modifications (e.g. PEN-PEG-MA-ePTFE) to yield polymers having effective antimicrobial activity. Further, and not to be limited by any particular theory, the effectiveness of PEN-PEG-MA-ePTFE may result from the increased surface area from which the PEN is exposed to the external environment; this increased surface area arrives from the provision of PEG having two different molecular weights (refer above) in fabricating the PEN-PEG-MA-ePTFE invention embodiment.

The above bacterial inhibition assay was quantified by measuring the absorbance (600 nm) of the five cultures described above. Figure AA illustrates the results of these experiments and shows that the lowest relative absorbance is detected for the culture exposed to the PEN-PEG-MA-ePTFE specimen, thus demonstrating the antibacterial activity of this specimen. It should be noted the above bacterial culture experiments were conducted using *Staphylococcus aureus*, which is a gram-positive species. The same set of experiments was conducted using the gram-negative bacterial species, *Pseudomonas aeruginosa*. Cultures of this bacteria with PEN-PEG-MA-ePTFE were turbid and had high relative absorbance values similar to cultures with the control ePTFE species (FIG. 8B). This result indicates that PEN attached to PEG-modified ePTFE surfaces is effective for controlling the proliferation of gram-positive bacteria. Furthermore, since it is well known that penicillins do not inhibit gram-negative bacteria, the above result (FIG. 8B, tube #4) demonstrates that the inhibition of *S. aureus* by PEN-PEG-MA-ePTFE is due to the antibiotic activity of PEN, and not some otherwise non-specific effect of the PEN-modified ePTFE.

It should be noted with the present invention that the amount of antibiotic attached to the ePTFE polymer is significantly less than the amount of antibiotic typically administered in solution. Despite this lower amount, the polymer-attached antibiotic is still very effective in inhibiting microbe growth, thereby demonstrating its effectiveness in preventing biofilm formation. This important functionality is likely due to the high mobility of the attached antibiotic molecules; such mobility is accomplished by phasing a molecular spacer between the substrate surface and the antibiotic molecules. When bacteria contact this modified surface, peptidoglycan cell wall synthesis is immediately interrupted by the antibiotic molecules, thus inhibiting the bacterial growth necessary for biofilm formation.

The above examples demonstrate that maleic anhydride and carboxylic acid groups can be chemically bonded to ePTFE surfaces with the provision of microwave plasma radiation. Maleic anhydride reacts with ePTFE surfaces through a $C=C$ bond opening of the maleic anhydride ring and its subsequent hydrolysis results in chemically attached carboxylic acid groups. The examples also demonstrate that PEN can be esterified onto PEG spacer groups that are attached to an ePTFE surface, and that the resulting PEN-modified polymer exhibits highly effective antimicrobial activity towards gram-positive bacteria. This approach, which is a non-limiting embodiment of the current invention, can serve as a general surface modification process for the development of polymeric surfaces with antimicrobial properties.

Example 4

Use of Amidation Reactions to Modify ePTFE Polymer Surfaces with Antibiotic

Figure 9:
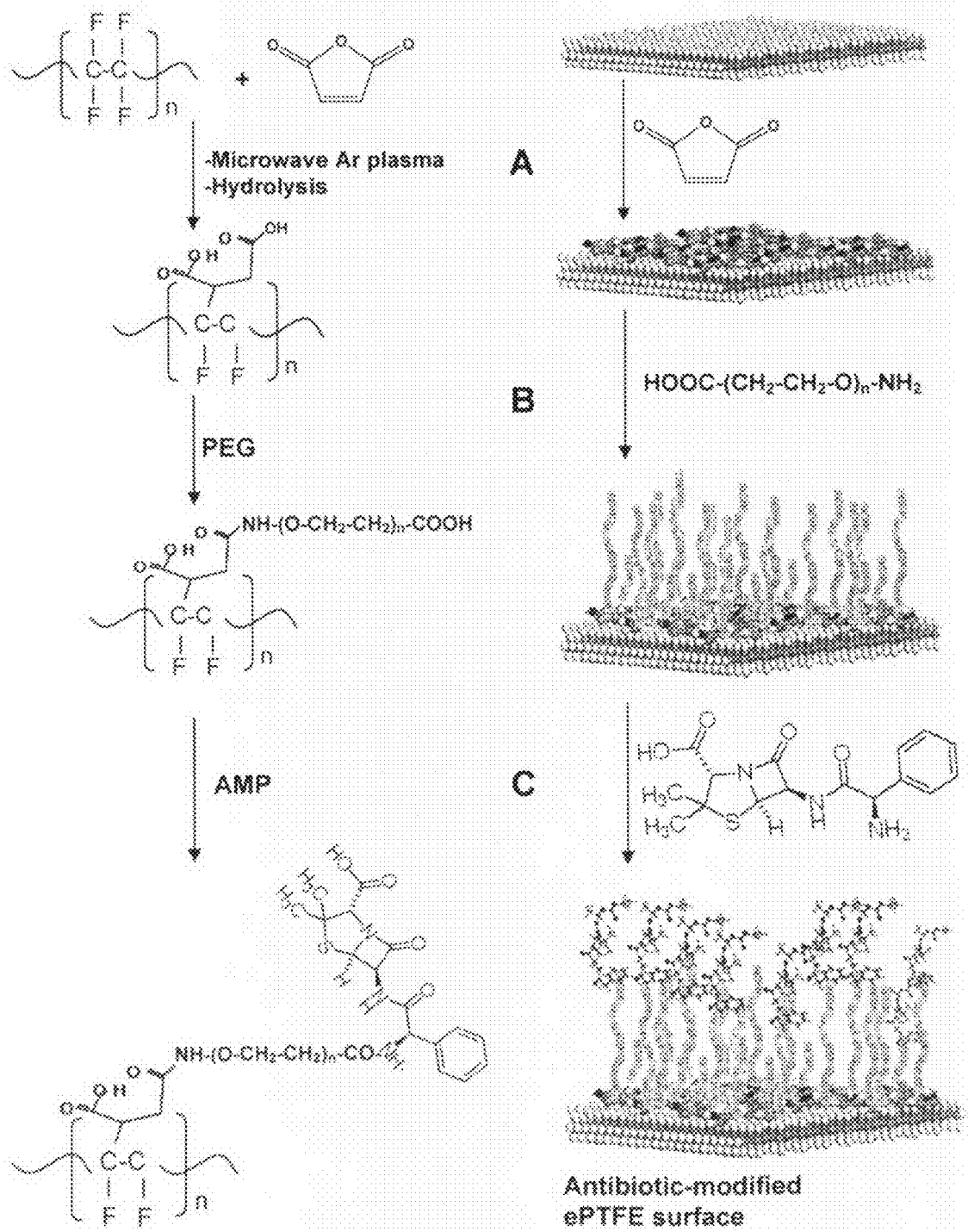
FIG. 9: Schematic diagram of surface reactions on ePTFE (left) and representation of ePTFE surface modifications (right): step A) microwave plasma reaction attaching MA to ePTFE followed by hydrolysis of attached MA to produce surface COOH groups; step B) attachment of heterobifunctional PEG (HOOC—(CH$_2$—CH$_2$—O)$_n$—NH$_2$) (this is a form of functionalized PEG) by an amidation reaction to acid groups; and step C) attachment of ampicillin (AMP) to heterobifunctional PEG by an amidation reaction to yield AMP-PEG-MA-ePTFE (example of an antibiotic-modified ePTFE surface). Refer to Example 4.

In this example, ePTFE was modified to have broad spectrum antimicrobial properties by attaching ampicillin (AMP) to MA-modified ePTFE through amidation reactions involving heterobifunctional PEG ($NH_2$— and COOH-terminated; formula=HOOC—$(CH_2—CH_2—O)_n$—$NH_2$) as the spacer group (refer to FIG. 9). ATR-FTIR revealed that covalent attachment of AMP to the PEG spacer via amide linkage diminishes the level of AMP hydrolysis from the surface. This example also shows that approximately 90% of AMP molecules remain on the AMP-PEG-MA-modified ePTFE surface after incubation in phosphate-buffered saline (PBS) solution at 37° C. for 24 hours. Quantitative analyses demonstrated that the highest antibiotic activity of AMP as attached to ePTFE was associated with solutions containing AMP-PEG-MA-ePTFE.

Experimental

To modify MA-ePTFE surfaces with AMP (Sigma Inc.), heterobifunctional PEG 2000 MW having COOH and $NH_2$ end-groups (JenKem Technology USA) was used as a flexible spacer between modified ePTFE surfaces and AMP. MA-ePTFE was first prepared as described in Example 1. Acid groups on the ePTFE surface resulting from the hydrolysis of the MA were first converted into acid chloride using thionyl chloride ($SOCl_2$) under reflux conditions at 65° C. for 9 hours. The sample was removed from the flask and washed with chloroform for one hour to eliminate excess thionyl chloride. The acid chloride ePTFE surfaces were then placed into a 0.5 M chloroform solution of heterobifunctional PEG 2000 MW. An amidation reaction was carried out in a sealed flask at room temperature for 18 hours; this reaction results in the condensation of surface COOH groups with $NH_2$ end-groups of the heterobifunctional PEG. A small amount (1-2 drops) of triethylamine was added into the reaction flask at the onset of the reaction to neutralize the hydrochloric acid generated during the reaction. Finally, the sample (PEG-MAePTFE) was washed with chloroform several times to remove unreacted (i.e. non-surface-linked) PEG.

The reaction of PEG-MA-ePTFE with AMP was conducted using another amidation reaction process. First, the acid groups of the PEG spacers were converted into acid chloride groups using thionyl chloride ($SOCl_2$) under reflux conditions at 65° C. for 9 hours. Excess thionyl chloride was removed as above, after which the acid chloride ePTFE surfaces were placed into a 0.2 M chloroform solution of AMP. An amidation reaction was performed as above, resulting in condensation of the surface PEG acid groups with the $NH_2$ groups of AMP molecules. The sample (AMP-PEG-MA-ePTFE) was then washed with chloroform several times to remove unreacted (i.e. non-surface-linked) AMP and dried for 24 hours prior to analysis.

In order to determine the anti-microbial activity of AMP-PEG-MA-ePTFE surfaces, gram-positive bacteria *Staphylococcus aureus* strain RN 6390, *Bacillus thuringiensis*, *Enterococcus faecalis*, and gram-negative bacteria *Escherichia coli*, *Pseudomonas putida*, and *Salmonella enterica* were grown overnight in LB broth. A series of specimens—ePTFE, MA-ePTFE, PEG-MA-ePTFE and AMP-PEG-MA-ePTFE—and a positive control were immersed into freshly incubated cultures of each of the above bacterial species and incubated at 37° C. for 5 hours. The anti-microbial activity of each specimen was determined by measuring the absorbance of the culture solution at 600 nm.

ATR-FTIR spectra were collected using a Bio-Rad FTS-6000 FTIR single-beam spectrometer set at a 4 $cm^{-1}$ resolution and equipped with a deuterated triglycine sulphate (DTGS) detector and a 45° face angle Ge crystal. Each spectrum represents 400 co-added scans ratioed against a reference spectrum obtained by recording 400 co-added scans of an empty ATR cell. All spectra were corrected of spectral distortions using Q-ATR software (Urban, 1996). An SEM Quanta FEI series 200 FEG was used to evaluate surface morphologies. All specimens were sputter-coated with gold and analyzed at a 45° angle with a scanning electron beam.

Internal reflection IR imaging (IRIRI) experiments were conducted on a Varian Stingray system with a Ge internal reflection element allowing spatial resolution of about 1 μm or better (Otts et al., 2002). This system consists of a Varian FTS 7000 spectrometer, a UMA 600 FTIR microscope with a focal plane array (FPA) image detector, and a semi-spherical Ge crystal. IRIRI images were collected using the sampling ratio of 2, rapid scan speed of 5 kHz, and 8 $cm^{-1}$ spectral resolution. Image processing was performed using Environment for Visualizing Images (ENVI) software (Research Systems, Inc., version 3.5). When appropriate, baseline correction algorithms were applied to compensate for baseline deviations which were accomplished by built-in application software supplied by GRAMS/AI v7.02 (Galactic Ind.) (Otts et al., 2002).

Analyses of the hydrolytic stability of AMP-PEG-MA-ePTFE surfaces were conducted by immersing a specimen in a PBS solution and incubating it at 37° C. After 0, 1-, 2-, 3-, 6-, 12-, 18-, and 24-hour exposure times, each specimen was dried and analyzed using ATR-FTIR spectroscopy.

Results and Discussion

While the attachment of PEN to ePTFE established the path forward in the modification of inert polymeric surfaces (refer to Example 2), this antibiotic, although widely used, is only effective against gram-positive bacteria. In an effort to develop antimicrobial polymeric surfaces that are effective against gram-positive and gram-negative bacteria, an antibiotic providing effectiveness against both these types of bacteria was attached to ePTFE. AMP represents such a broad spectrum antibiotic and has the structure shown below:

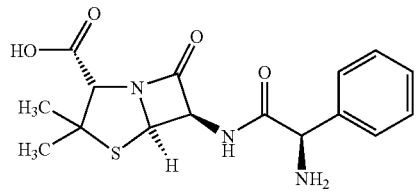

The studies of this example focused on the development of surface chemistry for attaching AMP to ePTFE and to determine its effectiveness, as attached to ePTFE, against a series of gram-positive and gram-negative bacteria.

Figure 10:
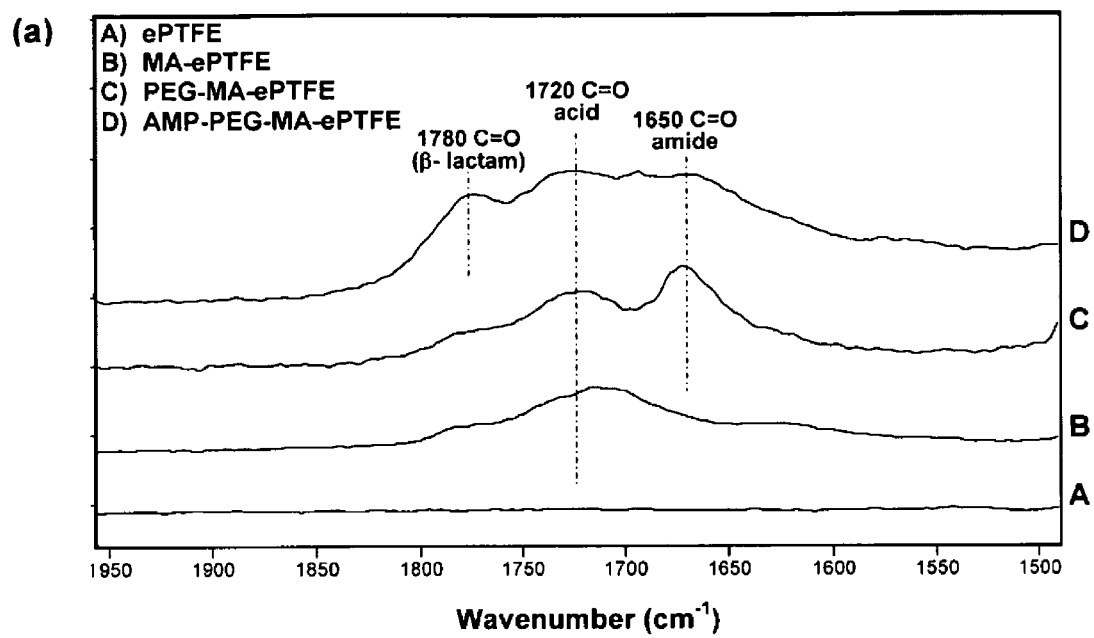
FIG. 10: ATR-FTIR spectra in the 1950-1450 cm$^{-1}$ (a) and 1300-1000 cm$^{-1}$ (b) regions of: A) ePTFE, B) MA-ePTFE, C) PEG-MA-ePTFE, and D) AMP-PEG-MA-ePTFE. Refer to Example 4.
Figure 10:
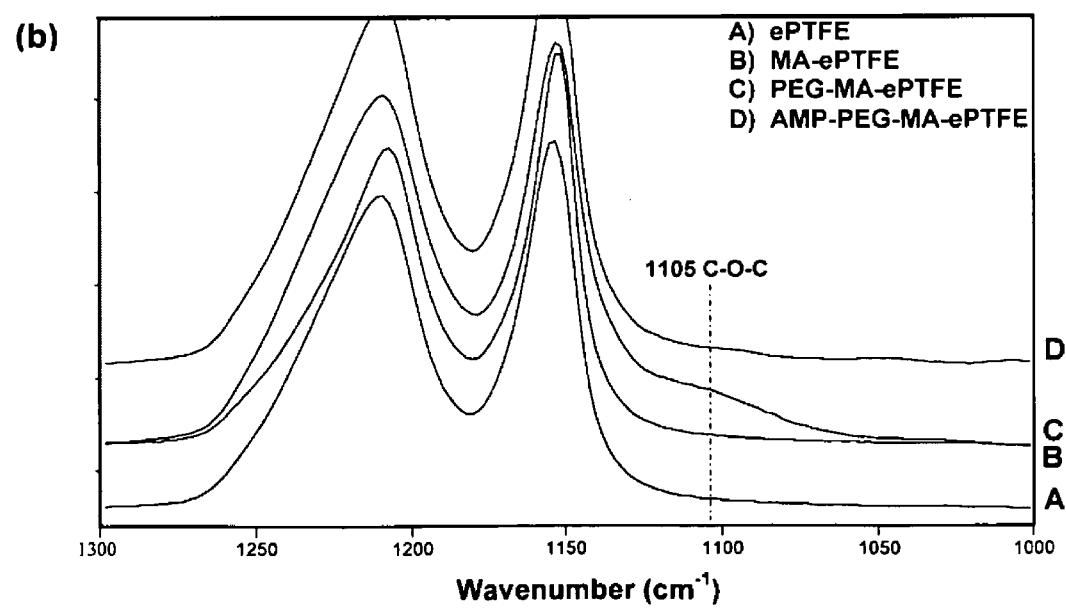

The first step shown in FIG. 9 (A) involves the attachment of MA, which upon hydrolysis generates COOH acid groups. To confirm COOH group formation, ATR-FTIR spectroscopy was utilized; spectra were recorded from the surface of ePTFE before and after plasma reactions (FIGS. 10 a and b; compare Traces A and B). For reference purposes, Trace A shows the spectrum of ePTFE, whereas Trace B represents the spectrum of ePTFE after microwave plasma reactions and hydrolysis (MA-ePTFE).

Although one could take advantage of the presence of the amine groups of AMP and react them directly with the COOH groups of hydrolyzed MA-ePTFE, this approach would anchor and thus immobilize AMP on the surface, thus making it less effective against microbial colonization and biofilm formation (Hollander et al., 2004; Roseeuw et al., 2003). To alleviate this issue, we utilized heterobifunctional $NH_2$— and COOH-terminated PEG. This innovative approach was employed to react the $NH_2$-end of heterobifunctional PEG with the MA-ePTFE surface COOH groups (FIG. 9 [B]), thus rendering a COOH-terminated flexible spacer that can be further modified with AMP.

In FIG. 10 (a and b), Traces A-C respectively show ATR-FTIR spectra of surfaces of ePTFE, MA-ePTFE, and PEG-MA-ePTFE. While Traces A and B serve as references, Trace C illustrates the presence of the 1105, 1650 and 1720 $cm^{-1}$ bands due to, respectively, C—O—C stretching, C=O amide, and C=O acid vibrations (Koenig, 1999; Pretsch et al., 2000; both these references are herein incorporated by reference in their entirety) resulting from amidation reactions between heterobifunctional PEG and surface COOH groups. These data show that heterobifunctional PEG is covalently attached to the ePTFE surface through amide linkage, as depicted in FIG. 9 (B).

The final step for flexibly attaching AMP to ePTFE involved an amidation reaction between PEG-MA-ePTFE and AMP, as illustrated in FIG. 9 (C). The spectroscopic analysis shown in Trace D of FIG. 10 (a and b) illustrates that AMP was attached to $NH_2$—PEG-MA-ePTFE surfaces via amide linkages as manifested by the presence of amide linkages between AMP and PEG (1650 $cm^{-1}$ band), and bands at 1720 and 1780 $cm^{-1}$ due to C=O acid and β-lactam stretching vibrations (Koenig, 1999; Pretsch et al., 2000), respectively.

Figure 11:
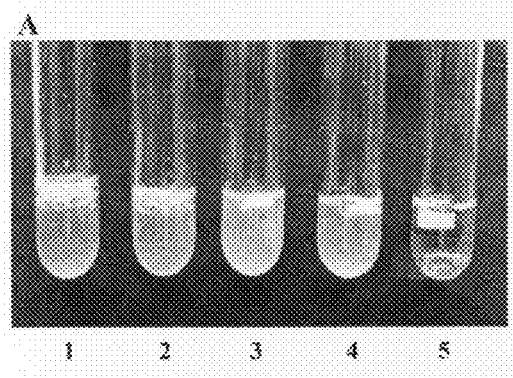
FIG. 11: Shown on the left are photographs of test tubes containing cultures of the gram-positive bacteria *Staphylococcus aureus* (A), *Enterococcus faecalis* (B), and *Bacillus thuringiensis* (C). For each of A-C, the treatments were as follows: control (tube 1), ePTFE (tube 2), MA-ePTFE (tube 3), PEG-MA-ePTFE (tube 4), and AMP-PEG-MA-ePTFE (tube 5). Shown on the right (A'-C') are optical densities (600 nm) of the cultures shown in A-C. Refer to Example 4.
Figure 11:
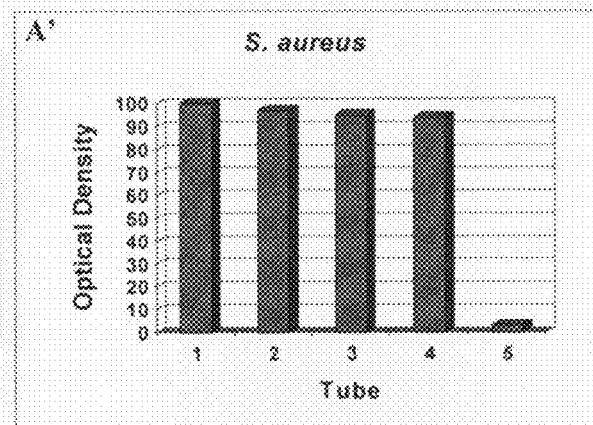
Figure 11:
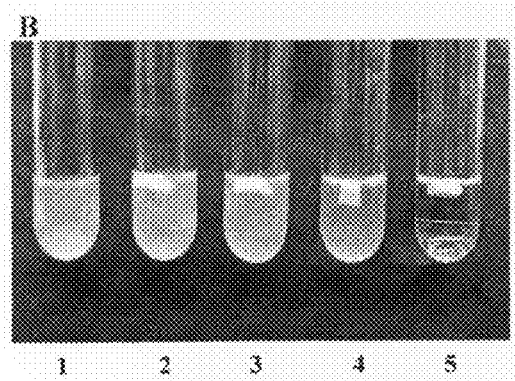
Figure 11:
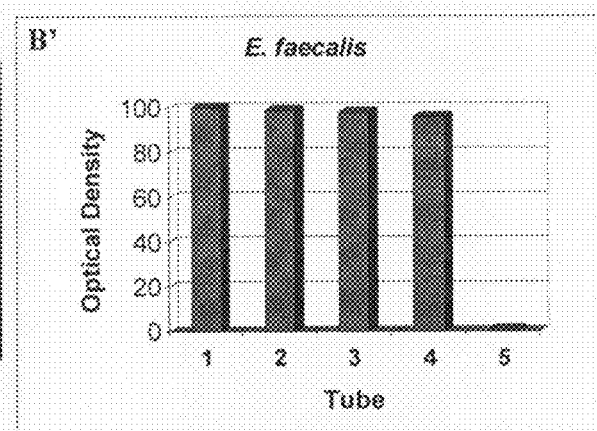
Figure 11:
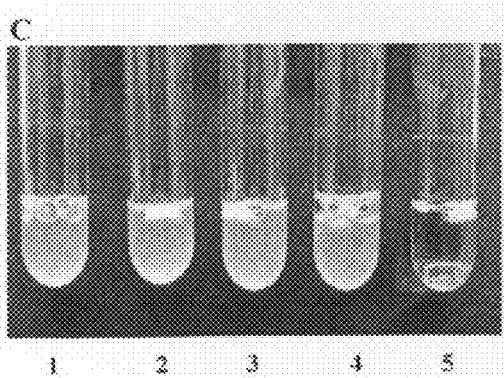
Figure 11:
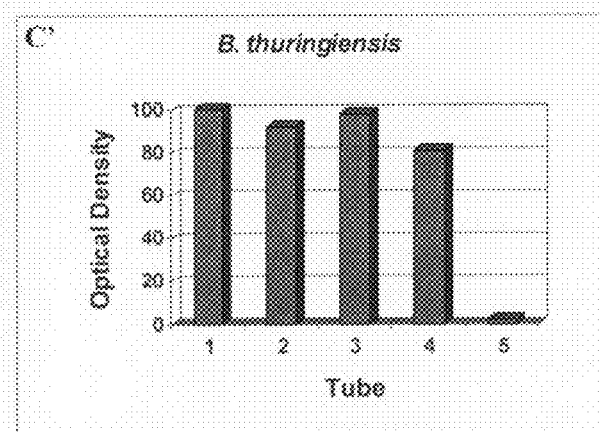
Figure 12:
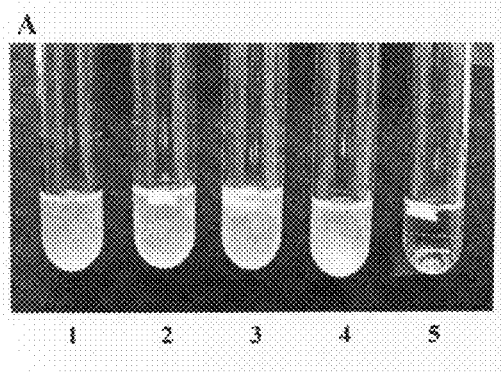
FIG. 12: Shown on the left are photographs of test tubes containing cultures of the gram-negative bacteria *Escherichia coli* (A), *Salmonella enterica* (B), and *Pseudomonas putida* (C). For each of A-C, the treatments were as follows: control (tube 1), ePTFE (tube 2), MA-ePTFE (tube 3), PEG-MA-ePTFE (tube 4), and AMP-PEG-MA-ePTFE (tube 5). Shown on the right (A'-C') are optical densities (600 nm) of the cultures shown in A-C. Refer to Example 4.
Figure 12:
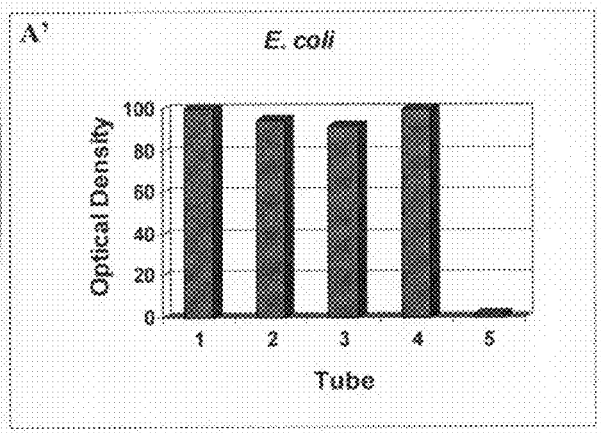
Figure 12:
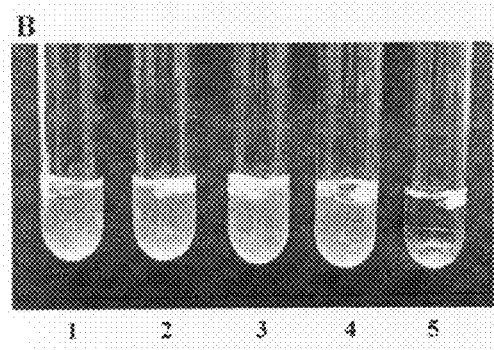
Figure 12:
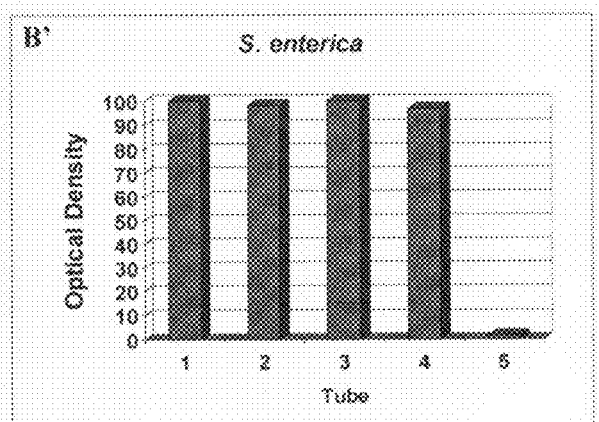
Figure 12:
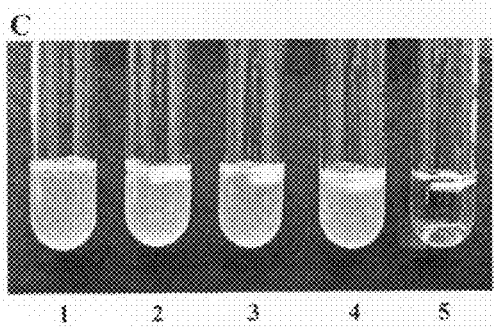
Figure 12:
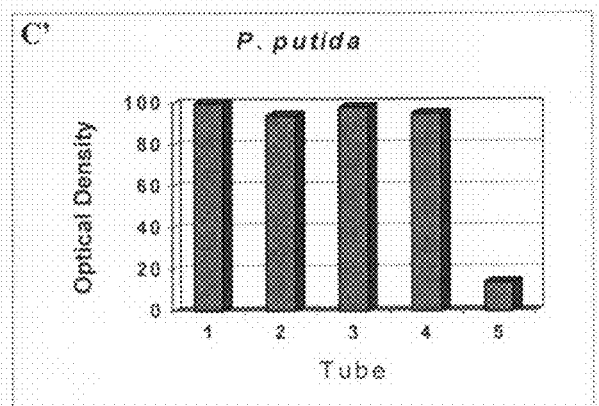

In an effort to determine if these surface modifications are effective against gram-positive and gram-negative bacteria, a series of experiments with six different bacteria were conducted (FIGS. 11 and 12). FIG. 11 (A-C) shows a set of photographs depicting turbidity differences of cultures containing gram-positive bacteria cultures, *S. aureus, E. faecalis,* and *B. thuringiensis*, respectively; culture turbidity was also quantified by absorbance measurements at 600 nm (A'-C'). For each bacterial species, cultures were grown alone as a control (tube 1), or with ePTFE (tube 2), MA-ePTFE (tube 3), PEG-MA-ePTFE (tube 4), or AMP-PEG-MA-ePTFE (tube 5). As seen with tube 5 for all three bacterial cultures, the presence of AMP on the ePTFE surface inhibited culture growth; this is demonstrated by the lack of turbidity of these cultures. In contrast, cultures 2-4 for the three bacterial growth experiments exhibited cloudiness, thereby indicating bacterial growth; these results (tubes 2-4) show that the inhibition of bacterial growth in tube 5 for each experiment is not due to a non-specific effect of ePTFE, MA and/or PEG.

The same series of experiments shown in FIG. 11 were conducted using the gram-negative bacteria *E. coli*, *S. enterica*, and *P. putida* (FIG. 12). FIG. 12 (A-C and A'-C') depicts that AMP-PEG-MA-ePTFE is capable of inhibiting these gram-negative bacteria. Again, this inhibition is specific to the AMP component of the modified ePTFE surface, since ePTFE, MA-ePTFE, and PEG-MA-ePTFE did not by themselves inhibit bacterial growth (tubes 2-4 for each bacteria tested in FIG. 4). FIGS. 3 and 4 demonstrate the broad-spectrum antimicrobial activity of AMP-PEG-MA-ePTFE.

Due to its unique mesh-like morphology, ePTFE provides a suitable bioenvironment for body tissue to form an interwinding network. How do the above surface modifications alter this morphology, and furthermore, do these surface reactions result in homogenous surface coverage? To address these issues, SEM and IRIRI were employed in parallel to analyze polymer surface morphology and the molecular make-up thereof. SEM images showed that there are morphological differences resulting from the surface reactions; fewer voids are observed when MA, PEG, and AMP are reacted to the surface (data not shown; refer to FIGS. 4 and 6 for comparable images).

The IRIRI arm of the dual analysis demonstrated that each of the modified surfaces—MA-ePTFE, PEG-MA-ePTFE, AMP-PEG-MA-ePTFE—has a homogenous chemical make-up (data not shown). This result was found by tuning to the bands (spectral band or region) characteristic of the COOH, C=O, $NH_2$, and C=O (lactam ring) groups within certain of these surfaces. Specifically, IRIRI images collected from non-modified ePTFE surfaces were obtained by tuning into the 1210 $cm^{-1}$ spectral band (C—F bond). Those images collected from MA-ePTFE (hydrolyzed) surfaces were obtained by tuning into the 1710 $cm^{-1}$ spectral band (C=O of acid group). Images collected from PEG-MA-ePTFE surfaces were obtained by tuning into the 1100 $cm^{-1}$ spectral band (C—O—C), as well as the 1900-1500 $cm^{-1}$ region, which contains the specific 1710 $cm^{-1}$ (C=O of acid group) and 1660 $cm^{-1}$ (C=O of amide bond) spectral bands. Finally, images collected from AMP-PEG-MA-ePTFE were obtained by tuning into the 1780 $cm^{-1}$ spectral region, which indicates the C=O bond of the AMP β-lactam ring. For each of the above surface species, the signature molecular groups thereof were detected throughout the entire surface with the exception of void areas where there is no material and therefore no IR bands.

Figure 13:
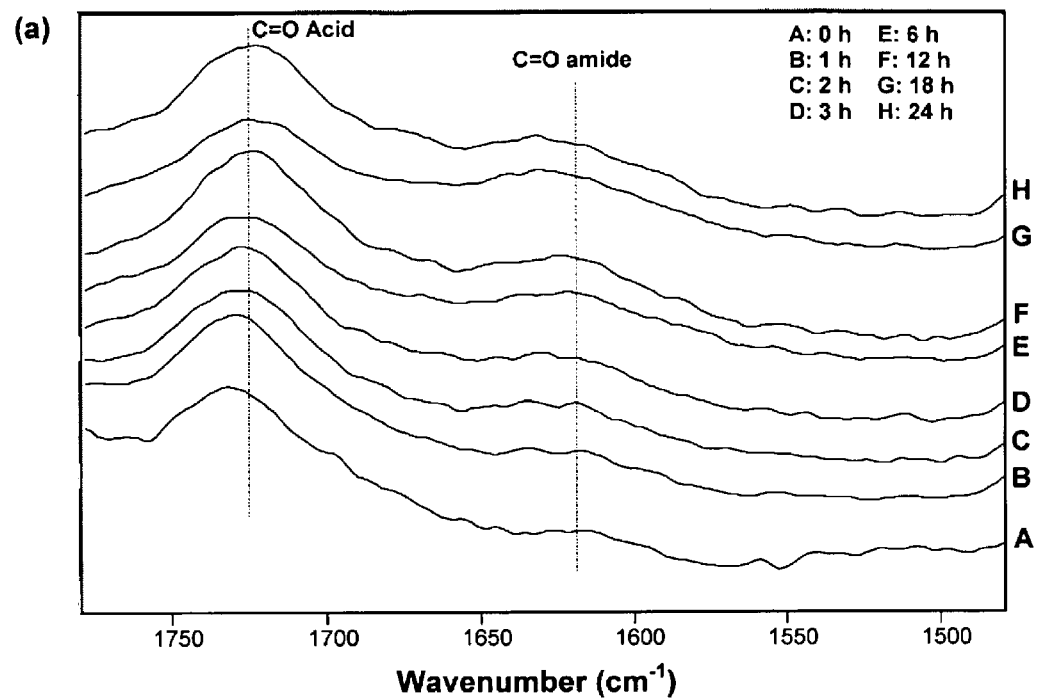
FIG. 13: (a) ATR-FTIR spectra in certain C=O regions recorded during 0-24 hours of exposure of AMP-PEG-MA-ePTFE to PBS solution at 37° C. The time periods of incubation were as follows: 0 h (A); 1 h (B); 2 h (C); 3 h (D); 6 h (E); 12 h (F); 18 h (G); 24 h (H). (b) Percent absorbance loss of the C=O amide (plot A, diamonds; refer to left ordinate) and AMP volume concentration loss (plot B, squares; refer to right ordinate), both plotted as a function of exposure time (hours) of AMP-PEG-MA-ePTFE to 37° C. PBS solution. Refer to Example 4.
Figure 13:
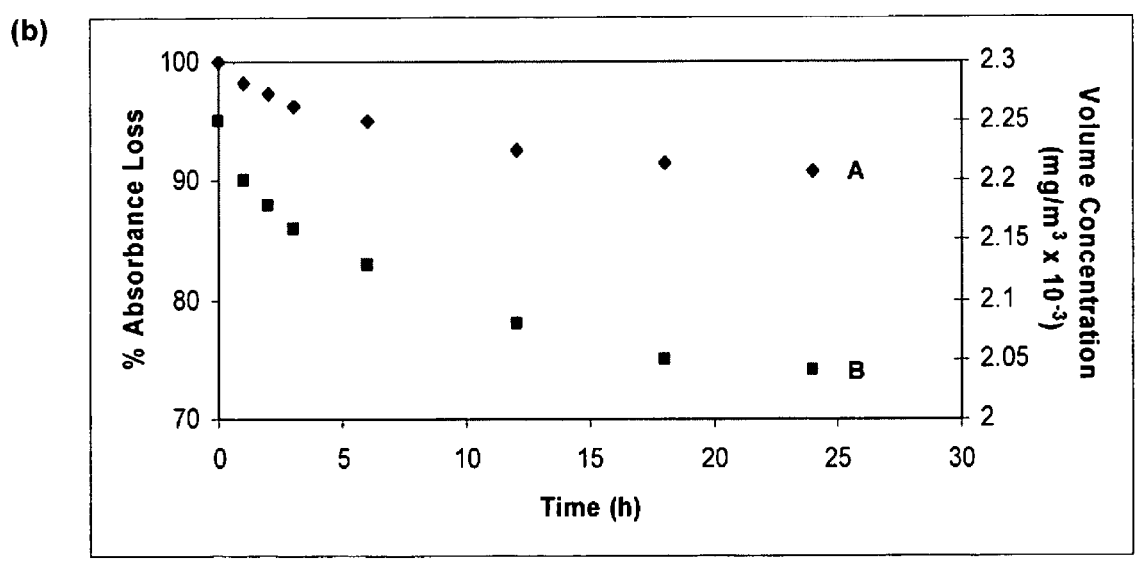

In a final analysis, the lability of AMP as it is bound to PEG spacers on ePTFE was tested. To determine the hydrolytic stability of these linkages, AMP-PEG-MA-ePTFE specimens were exposed to PBS solutions at 37° C. (normal human body temperature) for certain times and subsequently monitored for intensity changes in the spectral band indicative of the amide bond C=O group that participates in the amide bond between AMP and PEG. Since 37° C. is the optimal growth temperature of several human bacterial pathogens, it is of interest to know how well the AMP-modified surfaces maintain their structure at this temperature. FIG. 13 (a) illustrates a series of ATR-FTIR spectra for the AMP-PEG amide linkage C=O region recorded for AMP-PEG-MA-ePTFE at 37° C. Although this AMP linkage slightly decreases with incubation time, this decrease is only marginal given that the amide C=O spectral band retains approximately 90% of its initial absorbance after 24 hours (FIG. 13 [b, plot A]). Since ATR-FTIR experiments allow the quantification of the amount of AMP remaining on the surface, the absorption coefficient of the amide C=O groups was determined using Q-ATR algorithm, which in turn allowed the determination of AMP surface concentrations. As shown in FIG. 13 (b, plot B), the amount of AMP only falls from 2.25 $\mu g/m^3$ to 2.04 $\mu g/m^3$ (~10%) over the 24-hour exposure period, which is consistent with the ATR-FTIR AMP measurements. Thus, most of the AMP remains attached to the modified polymer surface to render it as antimicrobial.

Example 5

Producing Antimicrobial Polypropylene Surfaces

Surface reactions were performed on polypropylene (PP) in order to retard the growth of *S. aureus* and *E. coli* bacteria. Microwave plasma reactions in the presence of maleic anhydride (MA) caused acid groups to form on the surface of PP. These acid groups (carboxylic) were used in a reaction with a 400 and 600 molecular weight linear PEG mixture for preparing anti-*S. aureus* surfaces or in a reaction with 500 molecular weight linear diglycidyl-PEG for preparing anti-*E. coli* surfaces. The surface with the PEG mixture (400 and 600 MW PEG) was reacted with penicillin V (PEN) to create an antimicrobial surface that particularly targeted *S. aureus*. The surface with the glycidyl PEG was reacted with gentamicin (GEN), an aminoglycoside antibiotic, to create an antimicrobial surface that particularly targeted *E. coli*.

Surface morphological changes with both these types of surface modifications were monitored using scanning electron microscope (SEM) and spectroscopic analysis (ATR-FTIR). The latter analysis revealed the formation of ester linkages between PEN and PEG functionalities, and amide linkages between GEN and PEG functionalities. The PEN-PEG linkage thus represents another example of an antibiotic with a carboxylic group participates in an esterification reaction with PEG. The GEN-PEG linkage thus represents another example where an antibiotic with an amine group participates in an amidation reaction with a PEG species.

Antibacterial properties were evaluated by immersing the PEN- and GEN-modified PP into *S. aureus* and *E. coli* liquid cultures, respectively, and monitoring bacterial growth by measuring culture absorbances at 600 nm. The lowest *S. aureus* growth was observed for PEN-PEG-MA-PP, and the lowest *E. coli* growth was observed for GEN-PEG-MA-PP.

Experimental

Medical grade PP specimens were purchased from San Diego Plastics (San Diego, Calif.), cut to 1×1-cm squares, washed with acetone in an ultrasonic washer, and dried at room temperature. Plasma reactions were conducted using open reactor conditions; this process is known in the art. The PP substrate and 1 g of solid MA (Aldrich Chemical Co.), the latter of which had been grinded into a powder, were placed into the microwave reactor chamber and spaced 8.5 cm apart of each other. In a typical experiment, the reactor was evacuated to 150 mTorr, followed by purging it with Ar gas to reach a steady-state pressure of 250 mTorr at a flow rate of 4.0 mL/min. At this point, microwave radiation at 600 W of power with an output frequency of 2.45 GHz was turned on to induce plasma formation for 5 seconds. Under these conditions, the reaction chamber pressure increases continuously during the microwave plasma discharge. A vacuum was applied continuously to maintain pressure conditions during the experiment. Because monomeric and polymeric forms of MA are water soluble, in an effort to determine stability of the surface reactions and to ensure that the newly formed species are not physisorbed on the surface, the specimens were washed in water for 30 minutes, and stored in a desiccator under ambient conditions.

To convert acid groups (result from MA hydrolysis) on the PP surfaces to acid chloride, thionyl chloride under reflux conditions at 60° C. for 1 hour was employed. Upon completion the specimen was removed from the flask and washed with chloroform to eliminate excess thionyl chloride. The acid chloride PP surfaces were then placed into a chloroform solution of PEG (50% by volume) containing a 1:1 volume ratio of linear PEG 400 and 600 molecular weight. The esterification reaction was carried out in a sealed flask at room temperature for 18 hours. A small amount (1-2 drops) of tripropylamine was added into the reaction flask at the onset of the reaction to neutralize hydrochloric acid that was generated during the reaction. Each specimen was washed with chloroform several times to remove unreacted PEG, followed by a final wash with distilled water for 1 hour.

To modify PEG-MA-PP surfaces with PEN (Sigma Inc.), an esterification reaction using 4-(dimethylamino)-pyridine (DMAP) catalyst and dicyclohexyl-carbodiimide (DCC) coupling agent was conducted. The K salt of penicillin V (PEN V) (1.5 mmol) was dissolved in a small volume of water, cooled, and acidified with 0.1 N HCl. Precipitated PEN V was filtered and dried in a vacuum oven at room temperature for 1 hour. PEG-MA-PP specimens and DMAP (0.25 mmol) were placed into a 100-mL flask with 20 mL of methylene chloride. In the next step, dried PEN V was added to the mixture, then stirred and cooled in an ice-water bath. DCC (1.3 mmol) was added, and the mixture was continuously stirred for 4 hours. Upon removal, all specimens were washed in methylene chloride sequentially for 2 hours, dried for 24 hours, and analyzed as discussed above.

To determine antimicrobial activity of PEN-PEG-MA-PP surfaces, *S. aureus* (RN 6390) and *Pseudomonas aeruginosa* (ATCC, Rockville, Md.) were allowed to grow overnight in LB broth and King's medium, respectively. A series of specimens (PP, MA-PP, PEG-MA-PP, PEN-PEG-MA-PP, and PEN-PP) were immersed into freshly incubated cultures of each bacteria and incubated at 37° C. for 3-4 hours. Antimicrobial activity was determined by measuring the absorbance at 600 nm using a UV-vis spectrometer (Beckman DU-600).

All of the compositions or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope of the invention.

All patents and publications identified in this application are hereby incorporated by reference.

REFERENCES

Andreopoulos A G, Papaspyrides C D, Tsilibounidis S, *Biomaterials*, 1991, 12, 83.
Bae W S, Urban M W, *Langmuir*, 2006, submitted for publication.
Bae W S, Urban M W, *Langmuir*, 2004, 20, 8372.
Balazs D J, Triandafillu K, Wood P, Chevolot Y, Van Delden C, Harms H, Hollenstein C, Mathieu H J, *Biomaterials*, 2004, 25, 2139.
Bellamy L J, *The Infared Spectra of Complex Molecules* 3rd ed. In Chapman and Hall: London, 1975.
Bellon J M, Bujan J, Honduvilla N G, Hernando A, *Ann Vasc Surg*, 1993, 7, 549.
Catanese III J, Cooke D, Maas C, Pruitt L, *J Biomed Mater Res (Appl Biomater)*, 1999, 48, 187.
Colthup N B, Daly L H, Wiberley S E, *Introduction to Infrared and Raman Spectroscopy*. 2nd ed. Academic: New York, 1975.
DeHaan R L, *Nature*, 1971, 231, 85.
Dupuy F P, Savoldelli M, Robert A M P, Robert L, Legeais J M, Renard G J, *Biomed. Mater. Res.*, 2001, 56, 487.
Elbert D L, Hubbell J A, *Annu. Rev. Mater. Sci.*, 1996, 26, 365.
Frazer R Q, Byron R T, Osborne P B, Wes K P, *J. Long-Term Effects of Medical Implants*, 2005, 15, 629.
Gaboury S R, Urban M W, *Langmuir*, 1993, 9, 3225.
Hollander A, Thome J, Keusgen M, Degener I, Klein W, *Applied Surface Science*, 2004, 235, 145.
Huck W T S, *Nature Materials*, 2005, 4, 271.
Jardine S, Wilson J I B, *Plasma Process. Polym.*, 2005, 2, 328.
Johnell M, Larsson R, Siegbahn A, *Biomaterials*, 2005, 26, 1731.
Koenig J L, *Spectroscopy of Polymers*. 2nd ed. Elsevier Science Inc.: New York, 1999.
Kang E T, Tan K L, Kato K, Uyama Y, Ikada Y, *Macromolecules*, 1996, 29, 6872.
Kim H, Urban M W, *Langmuir*, 1998, 14, 7235.
Kroschwitz J I, *Polymers: Biomaterials and Medical Applications*. A Wiley-Interscience, John Wiley & Sons: New York, 1989.
Levesque S, Thibault J, Castonguay M, Gaudreault R C, Laroche G, *Colloids and Surfaces B: Biointerfaces*, 2002, 25, 205.
Mole B, *Plast Reconstruct Surg*, 1992, 90, 200.
Niwa M, Kawakami H, Kanno M, Nagaoka S, Kanamori T, Shinbo T, Kubota S, *J. Biomat Sci., Pol. Ed.* 2001, 12, 533.
Otts D B, Zhang P, Urban M W, *Langmuir*, 2002, 18, 6473.
Pena J, Vallet-Regi M, San Roman J, *J. Biomed Mater Res.*, 1997, 35, 129.
Pretsch E, Buhlmann P, Affolter C, *Structure Determination of Organic Compounds: Tables of Spectral Data*. 3rd Ed. Springer: N.Y., 2000.
Renard G, Cetinel B, Legeais J M, Savoldelli M, Durand J, Pouliquen Y, *J. Biomed Mater Res.*, 1996, 31, 193.
Rittgers S E, Garcia-Valdez C, McGuigan J A, *J Med Eng Technol*, 1985, 9, 1.
Roseeuw E, Coessens V, Balazuc A, Lagranderie M Chavarot P, Pessina A, Neri M G, Schacht E, Marchal G, Domurado D, *Antimicrobial Agents and Chemotherapy*, 2003, 47, 3435.
Schulze Nahrup J, Gao Z M, Mark J E, Sakr A, *Inter J. Pharmaceutics*, 2004, 270, 199.
Shalaby S W, *Biomedical Polymers*. Hanser: N.Y., 1994.
Streitweiser, Heathcock, *Introduction to Organic Chemistry*, 2.sup.nd ed., MacMillan Publishing Company: New York, 1981.

Strominger J, Park J T, Thompson R, *J. Biol. Chem.*, 1959, 234, 3263.

Swartbol P, Truedsson L, Parsson H, Norgren L, *J Biomed Mater Res.*, 1996, 32, 669.

Tokuyama T, Fujii S, Sato K, Abo M, Okubo A, *Anal. Chem.*, 2005, 77, 3309.

Urban M W, *Attenuated Total Reflectance Spectroscopy of Polymers Theory and Practice*. American Chemical Society: Washington, D.C., 1996.

Wang P, Tan K L, Kang E T, *J. Biomater. Sci. Pol. Ed.*, 2000, 11, 169.

Weber N, Caliebe J, Ziemer G, Wendel H P, *J. Biomat Sci. Pol. Ed.*, 2003, 14, 747.

Yang H, Lopina S, *J. Biomater. Sci. Pol. Ed.*, 2003, 14, 1043.

Yasuda H, *J. Macromol. Sci.-Chem.*, 1976, A10, 383.

Zalipsky S, Gilon C, Zilkha A, *Eur. Polym.*, 1983, 19, 1177.

Zhao Y, Urban M W, *Langmuir*, 1999, 15, 3538.

What is claimed is:

1. A method for modifying the surface of a polymer with a bio-active agent, comprising:
    a) providing an organic polymer;
    b) reacting the polymer with an anhydride, whereby anhydride groups are linked to the polymer surface;
    c) hydrolyzing the polymer surface-linked anhydride groups, whereby polymer surface-linked carboxylic acid groups are formed;
    d) reacting the polymer surface-linked carboxylic acid groups with polyalkylene glycol or functionalized polyethylene glycol (PEG) to effectively link polyalkylene glycol or functionalized PEG to the polymer surface; and
    e) reacting the polymer surface-linked polyalkylene glycol or functionalized PEG with a bio-active agent to covalently link the bio-active agent to the polymer surface;
    wherein the polymer surface is modified with the bio-active agent.

2. The method of claim 1, wherein the polymer is a polyolefin.

3. The method of claim 2, wherein the polymer comprises extended polytetrafluoroethylene (ePTFE).

4. The method of claim 2, wherein the polymer comprises polypropylene.

5. The method of claim 1, wherein the bio-active agent is an antibiotic agent.

6. The method of claim 5, wherein the antibiotic agent is a β-lactam antibiotic.

7. The method of claim 6, wherein the β-lactam antibiotic is ampicillin or a penicillin.

8. The method of claim 5, wherein the antibiotic agent is an aminoglycoside antibiotic.

9. The method of claim 8, wherein the aminoglycoside antibiotic is gentamicin.

10. The method of claim 1, wherein the anhydride comprises a ring structure.

11. The method of claim 10, wherein the anhydride is maleic anhydride.

12. The method of claim 1, wherein the polyalkylene glycol comprises two or more different molecular weights of polyalkylene glycol.

13. The method of claim 1, wherein the polyalkylene glycol comprises PEG.

14. The method of claim 13, wherein the PEG or functionalized PEG comprises species thereof of about 200 molecular weight and about 600 molecular weight.

15. The method of claim 13, wherein the PEG or functionalized PEG has a molecular weight range between about 100 and 2000.

16. The method of claim 1, wherein the functionalized PEG terminates at either end with an amine group or a carboxylic acid group.

17. The method of claim 16, wherein the functionalized PEG has the formula: COOH—PEG-NH$_2$.

18. The method of claim 17, wherein reacting step (d) comprises linking the functionalized PEG at the amine end to polymer surface-linked carboxylic acid groups through a first amidation.

19. The method of claim 18, wherein reacting step (e) comprises linking the functionalized PEG to the bio-active agent through a second amidation, wherein the bio-active agent is an antibiotic agent that comprises an amine group, and wherein the second amidation occurs between the amine group of the antibiotic agent and the carboxylic acid end of the functionalized PEG.

20. The method of claim 1, wherein reacting step (d) comprises linking the polyalkylene glycol or functionalized PEG to the surface-linked carboxylic acid groups through esterification.

21. The method of claim 1, wherein reacting step (e) comprises esterification of the bio-active agent to the polymer surface-linked polyalkylene glycol or functionalized PEG, wherein the bio-active agent is an antibiotic agent.

22. The method of claim 1, wherein the functionalized PEG is monoglycidyl or diglycidyl PEG.

23. A polymer having a surface modified with a bio-active agent, wherein the polymer surface comprises:
    a) an organic linker group comprising an ester moiety or an amide moiety, wherein the linker group is covalently bonded to the polymer, and wherein neither the ester moiety nor the amide moiety participate in the covalent bond between the linker group and the polymer;
    b) a polyalkylene glycol spacer that is in ester linkage or amide linkage to the organic linker group; and
    c) a bio-active group that is in ester linkage or amide linkage to the polyalkylene glycol spacer, wherein the ester or amide linkage between the bio-active group and polyalkylene glycol spacer is formed at the terminus of the polyalkylene glycol spacer that is not in linkage with the organic linker group;
    wherein the bio-active group is located most distally from the polymer.

24. The polymer of claim 23, wherein the polymer is an organic polymer.

25. The polymer of claim 24, wherein the polymer comprises ePTFE or polypropylene.

26. The polymer of claim 23, wherein the bio-active agent is an antibiotic agent.

27. The polymer of claim 26, wherein the antibiotic agent is a β-lactam antibiotic or an aminoglycoside antibiotic.

28. The polymer of claim 23, wherein the polyalkylene glycol spacers comprise two or more different molecular weights of polyalkylene glycol.

29. The polymer of claim 23, wherein the polyalkylene glycol spacers comprise polyethylene glycol (PEG).

30. The polymer of claim 29, wherein the PEG has a molecular weight range between about 100 and 2000.

* * * * *